United States Patent
Mou et al.

(10) Patent No.: US 12,274,815 B2
(45) Date of Patent: Apr. 15, 2025

(54) METHOD OF PREVENTING AND HANDLING INDOOR AIR POLLUTION

(71) Applicant: Microjet Technology Co., Ltd., Hsinchu (TW)

(72) Inventors: Hao-Jan Mou, Hsinchu (TW); Ching-Sung Lin, Hsinchu (TW); Chin-Chuan Wu, Hsinchu (TW); Chi-Feng Huang, Hsinchu (TW); Yung-Lung Han, Hsinchu (TW); Tsung-I Lin, Hsinchu (TW); Chin-Wen Hsieh, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 652 days.

(21) Appl. No.: 17/410,637

(22) Filed: Aug. 24, 2021

(65) Prior Publication Data

US 2022/0118144 A1    Apr. 21, 2022

(30) Foreign Application Priority Data

Oct. 16, 2020    (TW) .................................. 109136005

(51) Int. Cl.
  *A61L 9/014*    (2006.01)
  *A61L 9/20*    (2006.01)
  *A61L 9/22*    (2006.01)

(52) U.S. Cl.
  CPC .............. *A61L 9/014* (2013.01); *A61L 9/205* (2013.01); *A61L 9/22* (2013.01);
  (Continued)

(58) Field of Classification Search
  CPC . A61L 9/014; A61L 9/205; A61L 9/22; A61L 2209/111; A61L 2209/14; A61L 2209/16; A61L 2209/22
  See application file for complete search history.

(56) References Cited

U.S. PATENT DOCUMENTS

| | | | |
|---|---|---|---|
| 2011/0197770 A1* | 8/2011 | Yun ....................... | F24F 1/0071 |
| | | | 55/438 |
| 2018/0147526 A1* | 5/2018 | Meirav .............. | B01D 53/0438 |
| | (Continued) | | |

FOREIGN PATENT DOCUMENTS

| | | |
|---|---|---|
| CA | 2 990 519 A1 | 4/2019 |
| CN | 103267328 A | 8/2013 |
| | (Continued) | |

OTHER PUBLICATIONS

Landscape Plants, Rhus chinensis (Year: 2020).*

*Primary Examiner* — Sean E Conley
*Assistant Examiner* — Brendan A Hensel
(74) *Attorney, Agent, or Firm* — Birch, Stewart, Kolasch & Birch, LLP

(57) ABSTRACT

A method of preventing and handling indoor air pollution is disclosed and includes: providing a portable gas detection device and plural gas exchangers allowed to inhale outdoor gas, purify and filter the inhaled gas, and introduce the inhaled gas into the indoor space, wherein an air pollutant in the gas within the indoor space is exported out to the outdoor for exchanging; disposing 1~50 gas exchangers within the indoor space, wherein the gas exchangers have an exported airflow rate of 200~1600 CADR, and the indoor space has a volume of 247.5~1650 m$^3$; and remotely controlling the gas exchangers to enable filtration, purification and gas exchange by the portable gas detection device when the portable gas detection device detects an air pollutant in the indoor space, to reduce the air pollutant in the indoor space to a safe detection value within 10 minutes, and achieve a clean, safe and breathable condition.

20 Claims, 24 Drawing Sheets

(52) U.S. Cl.
CPC ...... *A61L 2209/111* (2013.01); *A61L 2209/14* (2013.01); *A61L 2209/16* (2013.01); *A61L 2209/22* (2013.01)

(56) References Cited

U.S. PATENT DOCUMENTS

| | | | | |
|---|---|---|---|---|
| 2018/0290095 | A1* | 10/2018 | Wei | F24F 8/80 |
| 2019/0137378 | A1* | 5/2019 | Qi | A61L 9/015 |
| 2020/0400136 | A1* | 12/2020 | Pinkerton | F04F 5/16 |
| 2022/0072185 | A1* | 3/2022 | Miller | A61L 9/20 |

FOREIGN PATENT DOCUMENTS

| | | |
|---|---|---|
| CN | 105352095 A | 2/2016 |
| CN | 206531176 U | 9/2017 |
| CN | 110375399 A | 10/2019 |
| CN | 111195454 A | 5/2020 |
| JP | 2013-124788 A | 6/2013 |
| TW | M553418 U | 12/2017 |

\* cited by examiner

METHOD OF PREVENTING AND HANDLING INDOOR AIR POLLUTION

FIELD OF THE INVENTION

The present disclosure relates to a method of preventing and handling indoor air pollution, and more particularly to a method applicable to an indoor space by using a portable gas detection device and a plurality of gas exchangers to clean the gas in the indoor space.

BACKGROUND OF THE INVENTION

In recent, people pay more and more attention to the air quality around our daily lives. Particulate matter (PM), such as PM1, PM2.5, PM10, carbon dioxide, total volatile organic compounds (TVOC), formaldehyde and even the suspended particles, the aerosols, the bacteria, the viruses, etc. contained in the air are all exposed in the environment and might affect the human health, and even endanger the life seriously. It is worth noting that the problem of gas pollution in the indoor space has gradually attracted people's attention. Therefore, providing a solution for air purification by purifying and promoting the air quality to prevent from breathing harmful gases in the indoor environment, monitor the indoor air quality in real time anytime and anywhere, and purify the indoor air quickly when the indoor air quality is poor, which is an issue of concern developed in the present disclosure.

SUMMARY OF THE INVENTION

An object of the present disclosure provides a method of preventing and handling indoor air pollution. A portable gas detection device is utilized to monitor the air quality in the indoor environment at any time, transmit a signal to a gas exchanger, and operate the gas exchanger in accordance with the air quality of the environment detected by the portable gas detection device. If the air quality is poor, a plurality of gas exchangers are actuated after receiving the signal of poor air quality, so as to purify the air quality of the environment detected by the portable gas detection device by the gas exchangers. The gas exchanger includes a purification unit combined with a gas guider, which can export a gas at a specific airflow amount, to allow the purification unit to filter and obtain a purified gas. In addition, the gas guider constantly controls the exported airflow rate ranged from 200 clean air output ration (CADR) to 1600 CADR within 10 minutes, and 1~50 gas exchangers are provided in the indoor space, so that the air pollutant in the indoor space can be reduced under a safe detection value, and allow the gas to exchange into a safe and breathable condition. Moreover, when PM1, PM2.5, PM10, carbon dioxide, total volatile organic compounds (TVOC), formaldehyde and even the suspended particles, the aerosols, the bacteria and the viruses contained in the air is too high, it is available to obtain a real-time information, issue an alarm, and purify the indoor air immediately, so as to maintain good air quality.

In accordance with an aspect of the present disclosure, a method of preventing and handling indoor air pollution is provided for implementing in an indoor space and includes: a) providing a portable gas detection device and a plurality of gas exchangers for implementing in the indoor space, wherein the plurality of gas exchangers are allowed to inhale outdoor gas, purify and filter the inhaled gas, and introduce the inhaled gas into the indoor space, wherein an polluted air in the indoor space is exported and exchanged out to the outdoor; b) disposing 1~50 gas exchangers within the indoor space, wherein the gas exchangers have an exported airflow rate ranged from 200 clean air output ration (CADR) to 1600 CADR, and the indoor space has a volume of 247.5~1650 $m^3$; and c) remotely controlling at least one of the gas exchangers to enable filtration, purification and gas exchange procedure by the portable gas detection device, as the portable gas detection device detects an air pollutant in the indoor space in real time, to reduce the air pollutant in the gas within the indoor space to a safe detection value within 10 minutes, so that the gas contain air pollutant in the indoor space is exchanged to achieve a clean, safe and breathable condition.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
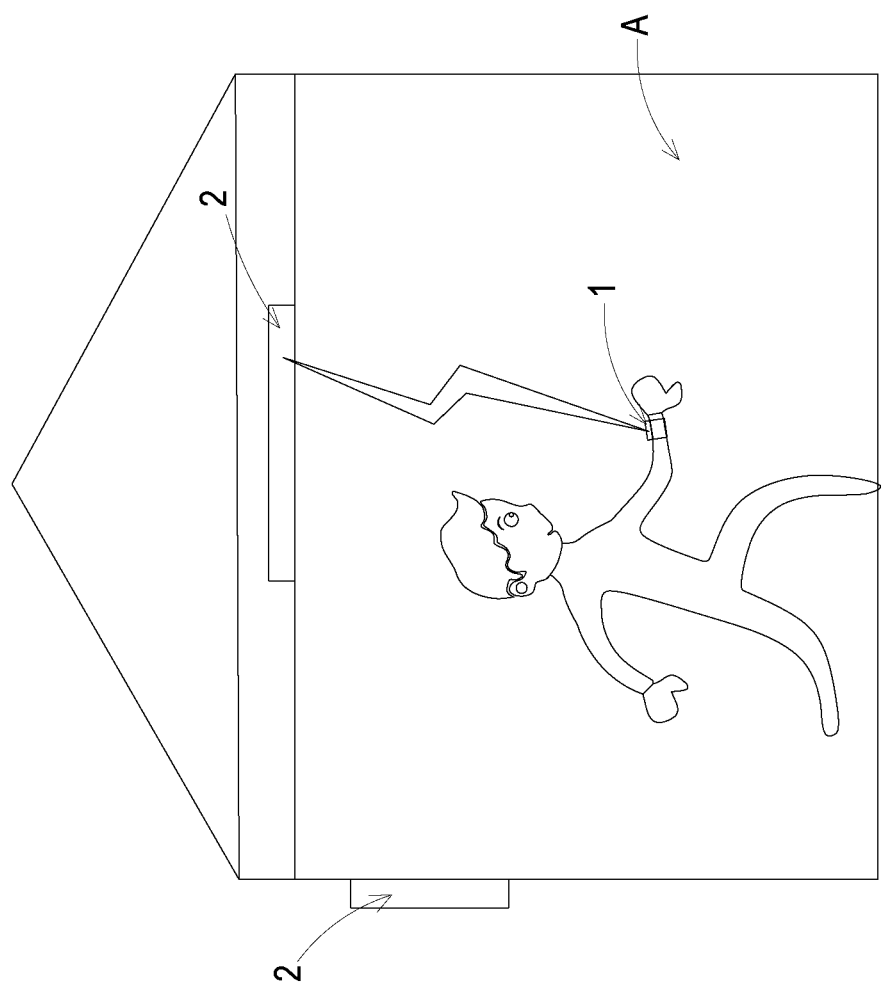
FIG. 1A is a schematic diagram of implementing a method of preventing and handling indoor air pollution according to an embodiment of the present disclosure.

Please refer to FIG. 1A. The present disclosure provides a method of preventing and handling indoor air pollution to implement in an indoor space A and includes a) providing a portable gas detection device 1 and a plurality of gas exchangers 2 for implementing in the indoor space A, wherein the plurality of gas exchangers 2 are allowed to inhale outdoor gas, purify and filter the inhaled gas, introduce the inhaled gas into the indoor space A, wherein an air pollutant in the indoor space A is exchanged and exported to the outdoor environment; b) disposing 1 to 50 gas exchangers 2 within the indoor space A, wherein the gas exchangers 2 have an exported airflow rate ranged from 200 clean air output ration (CADR) to 1600 CADR, and the indoor space has a volume of 247.5~1650 m$^3$; and c) remotely controlling at least one of the gas exchangers 2 to enable filtration, purification and gas exchange procedure by the portable gas detection device 1 when the portable gas detection device 1 detects an air pollutant in the indoor space in real time, so as to reduce the air pollutant in the gas within the indoor space A to a safe detection value within 10 minutes, so that the gas contain air pollutant in the indoor space A can be exchanged to achieve a clean, safe and breathable condition.

In the embodiment, the exported airflow rate of the gas exchanger 2 is 800 CADR, but not limited thereto. In other embodiments, the exported airflow rate of the gas exchanger 2 is ranged from 200 CADR to 1600 CADR. Moreover, in the embodiment, the volume of the indoor space A is 82.5 m$^3$. The volume of the indoor space A is calculated with a volume of 33.06 square meters×2.5 meters high, but not limited thereto. Preferably but not exclusively, in other embodiments, the volume of the indoor space A is ranged from 247.5 m$^3$ to 1650 m$^3$ and is adjustable according to the practical requirements. Notably, in the embodiment, there are 1~50 gas exchangers 2 disposed within the indoor space A for implementing. The number of the gas exchangers 2 is based on the corresponding exported airflow rate and the volume of the indoor space A, so as to exchange the air in the indoor room A within a certain operation time to achieve a clean air condition, but the present disclosure is not limited thereto. In other embodiments, the number of the gas exchangers 2, the exported airflow rate, the volume of the indoor space A and the operation time are all adjustable according to the practical requirements. Preferably but not exclusively, the corresponding relationship thereof can be referred to Table 1.

TABLE 1

| Number of the gas exchangers | | Volume of the indoor space A | |
|---|---|---|---|
| | | 247.5 (m$^3$) (99 m$^2$ × 2.5 m) | 1650 (m$^3$) (330 m$^2$ × 2.5 m) |
| Exported airflow rate | 200 CADR | 8 sets | 50 sets |
| | 800 CADR | 2 set | 13 sets |
| | 1600 CADR | 1 set | 7 sets |

Table 1 shows the relationship between the numbers of the gas exchangers 2, the exported airflow rate and the volume of the indoor space A when the gas exchangers 2 are operated within 10 minutes.

In the embodiment, the gas exchanger 2 has the exported airflow rate of 800 CARD, and the volume of the indoor space A is ranged from 247.5 m$^3$ to 1650 m$^3$. There are 2~13 sets of the gas exchangers 2 disposed within the indoor space A, but not limited thereto. In other embodiment, the exported airflow rate, the volume of the indoor space A and the corresponding number of the gas exchangers 2 can be adjusted according to the practical requirements.

In addition, notably, the air pollutant in the gas within the indoor space A is selected from the group consisting of particulate matter (PM), such as PM1, PM2.5 and PM10, carbon dioxide CO2, total volatile organic compounds (TVOC), formaldehyde, bacteria, virus and a combination thereof. Within 1 minute to 10 minutes, the gas exchangers 2 reduce the air pollutant in the gas within the indoor space A to a safe detection value, for example, the PM2.5 is less than 10 μg/m$^3$, the PM10 is less than 75 μg/m$^3$, the carbon dioxide content is less than 1000 ppm, the total volatile organic compounds (TVOC) is less than 0.56 ppm, the formaldehyde content is less than 0.08 ppm, the amount of bacteria is less than 1500 CFU/m$^3$, and the amount of fungi is less than 1000 CFU/m$^3$.

Figure 1B:
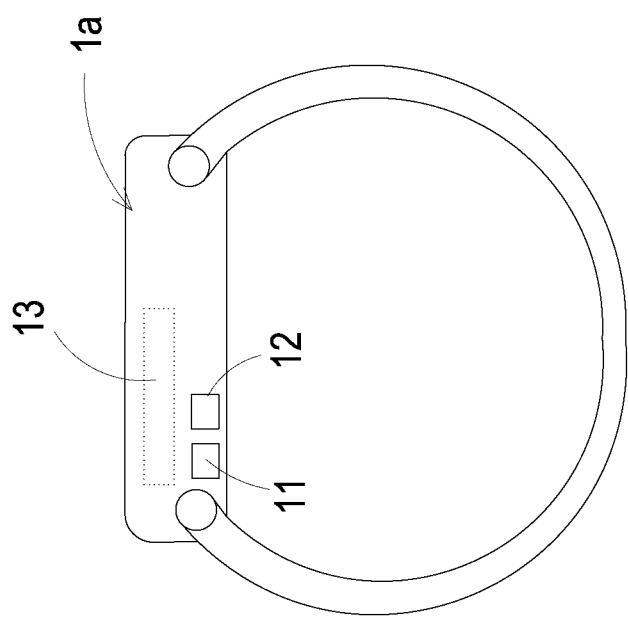
FIG. 1B is a schematic diagram illustrating a portable gas detection device according to an embodiment of the present disclosure.

Please refer FIG. 1B. In the embodiment, the portable gas detection device 1 includes a main body 1a having at least one inlet 11, at least one outlet 12 and a gas detection module 13. Preferably but not exclusively, the portable gas detection device 1 is a smart watch or a smart bracelet, which includes a main body 1a. In the embodiment, the main body 1a includes at least one inlet 11, at least one outlet 12 and a gas detection module 13. In the embodiment, the main body 1a has one inlet 11 and one outlet 12, but not limited thereto.

Please refer to FIGS. 2A to 2C, FIGS. 3A to 3B, FIG. 4 and FIGS. 5A to 5B. The gas detection module 13 includes a piezoelectric actuator 132 and at least one sensor 135. The gas outside the main body 1a is inhaled through the inlet 11 and discharged out through the outlet 12, and the introduced gas is detected by the sensor 135 for obtaining gas information. In the embodiment, the gas detection module 13 includes a base 131, a piezoelectric actuator 132, a driving circuit board 133, a laser component 134, a particulate sensor 135 and an outer cover 136. The base 131 includes a first surface 1311, a second surface 1312, a laser loading region 1313, a gas-inlet groove 1314, a gas-guiding-component loading region 1315 and a gas-outlet groove 1316. In the embodiment, the first surface 1311 and the second surface 1312 are two surfaces opposite to each other. In the embodiment, the laser loading region 1313 is hollowed out from the first surface 1311 to the second surface 1312. The gas-inlet groove 1314 is concavely formed from the second surface 1312 and disposed adjacent to the laser loading region 1313. The gas-inlet groove 1314 includes a gas-inlet 1314a and two lateral walls. The gas-inlet 1314a is in communication with an environment outside the base 131, and is spatially corresponding in position to an inlet opening 1361a of the outer cover 136. A transparent window 1314b is opened on the two lateral walls and is in communication with the laser loading region 1313. Therefore, the first surface 1311 of the base 131 is covered and attached by the outer cover 136, and the second surface 1312 is covered and attached by the driving circuit board 133. Thus, the gas-inlet groove 1314 and the driving circuit board 133 collaboratively define an inlet path.

In the embodiment, the gas-guiding-component loading region 1315 mentioned above is concavely formed from the second surface 1312 and in communication with the gas-inlet groove 1314. A ventilation hole 1315a penetrates a bottom surface of the gas-guiding-component loading region 1315. In the embodiment, the gas-outlet groove 1316 includes a gas-outlet 1316a, and the gas-outlet 1316a is spatially corresponding to the outlet opening 1361b of the outer cover 136. The gas-outlet groove 1316 includes a first section 1316b and a second section 1316c. The first section 1316b is concavely formed on a region out from the first surface 1311 spatially corresponding to a vertical projection area of the gas-guiding-component loading region 1315. The second section 1316c is hollowed out from the first surface 1311 to the second surface 1312 in a region where the first surface 1311 is misaligned with the vertical projection area of the gas-guiding-component loading region 1315 and extended therefrom. The first section 1316b and the second section 1316c are connected to form a stepped structure. Moreover, the first section 1316b of the gas-outlet groove 1316 is in communication with the ventilation hole 1315a of the gas-guiding-component loading region 1315, and the second section 1316c of the gas-outlet groove 1316 is in communication with the gas-outlet 1316a. In that, when first surface 1311 of the base 131 is attached and covered by the outer cover 136, and the second surface 1312 of the base 131 is attached and covered by the driving circuit board 133. Thus, the gas-outlet groove 1316, the outer cover 136 and the driving circuit board 133 collaboratively define an outlet path.

Figure 2A:
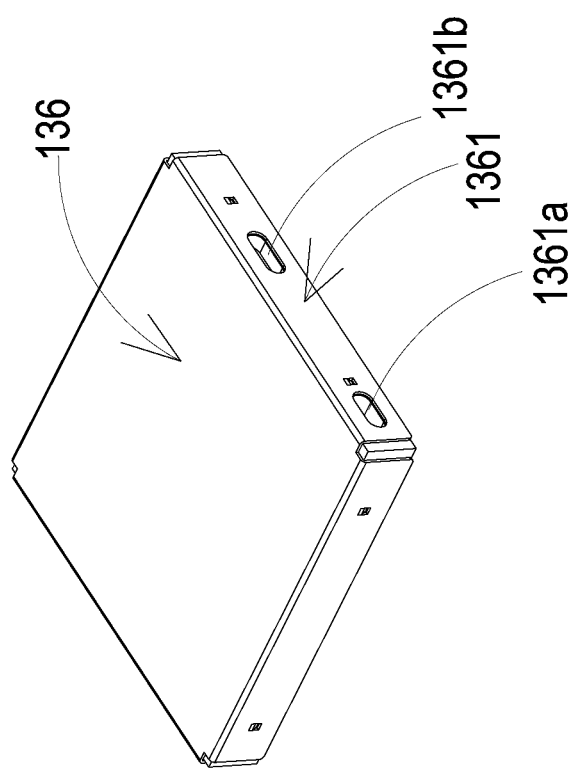
FIG. 2A is a schematic view illustrating the gas detection device according to the embodiment of the present disclosure.
Figure 2B:
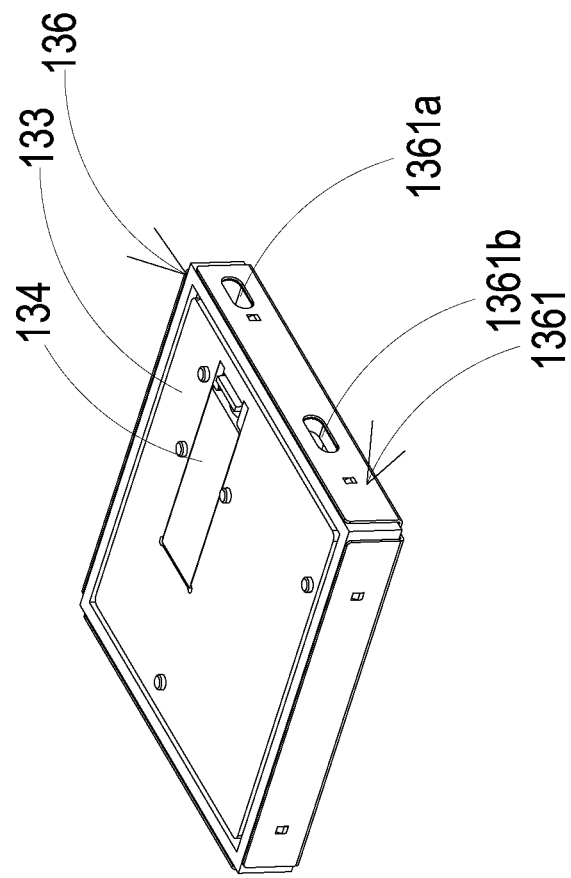
FIG. 2B is a schematic view illustrating the gas detection device according to the embodiment of the present disclosure from another perspective angle.
Figure 2C:
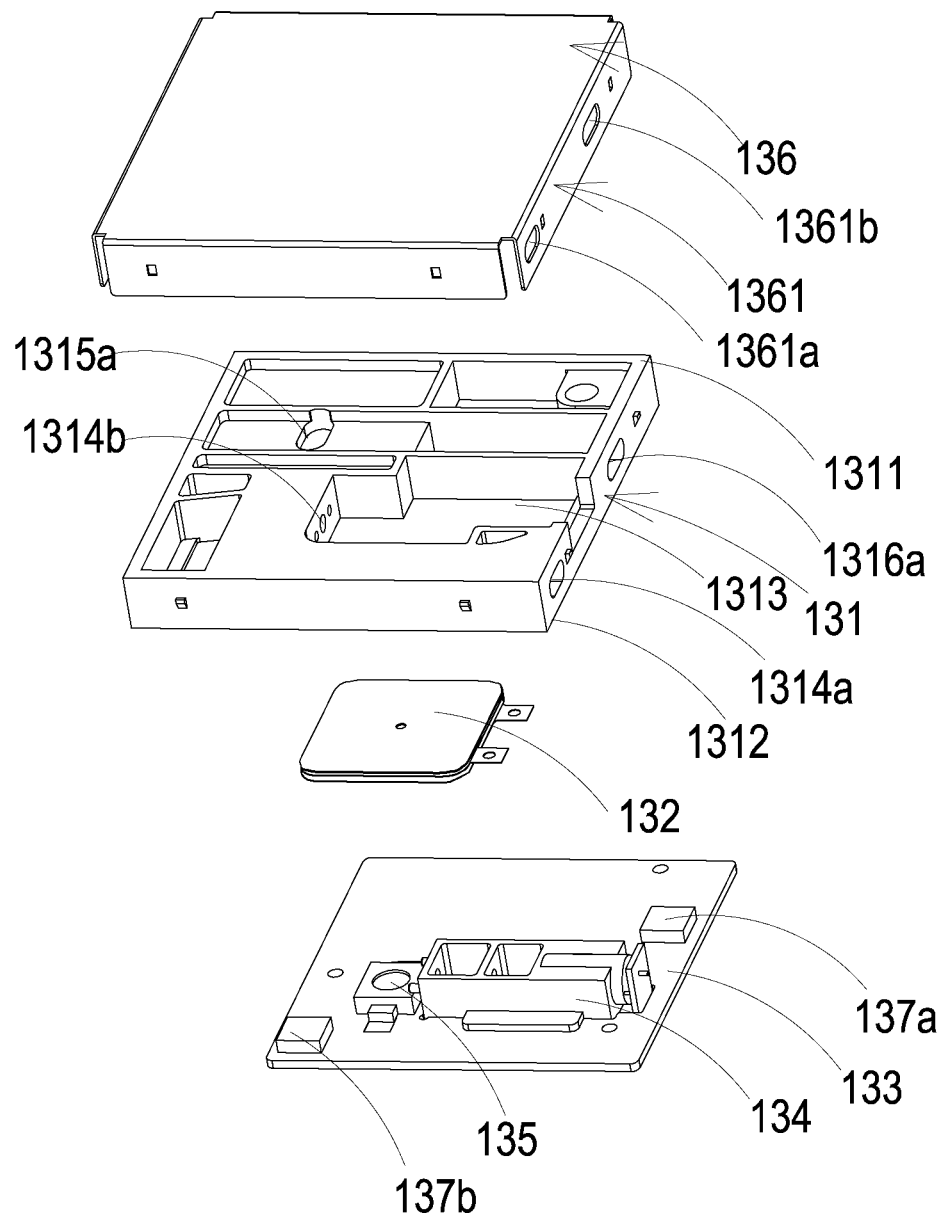
FIG. 2C is an exploded view illustrating the gas detection device according to the embodiment of the present disclosure.
Figure 3A:
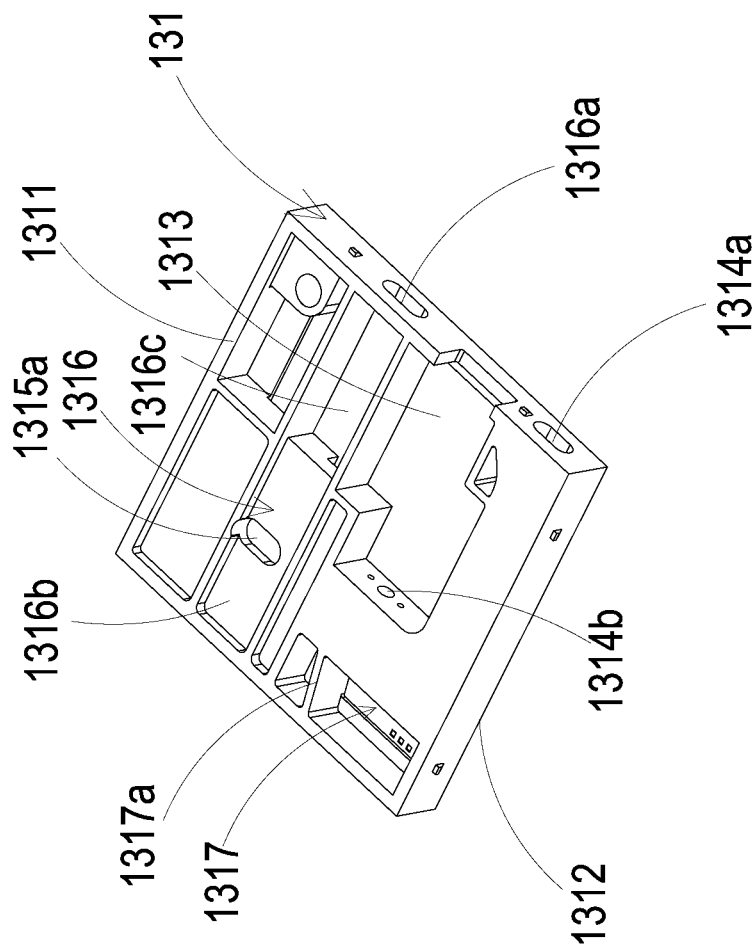
FIG. 3A is a schematic view illustrating a base of the gas detection device in FIG. 2C.
Figure 3B:
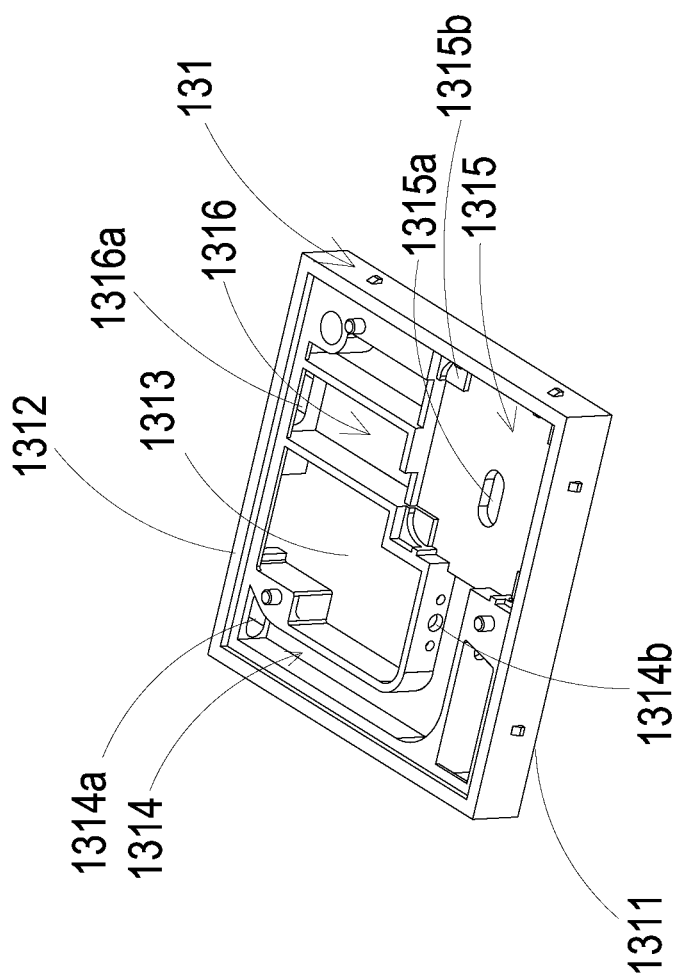
FIG. 3B is a schematic rear view illustrating the base of the gas detection device in FIG. 2C.
Figure 4:
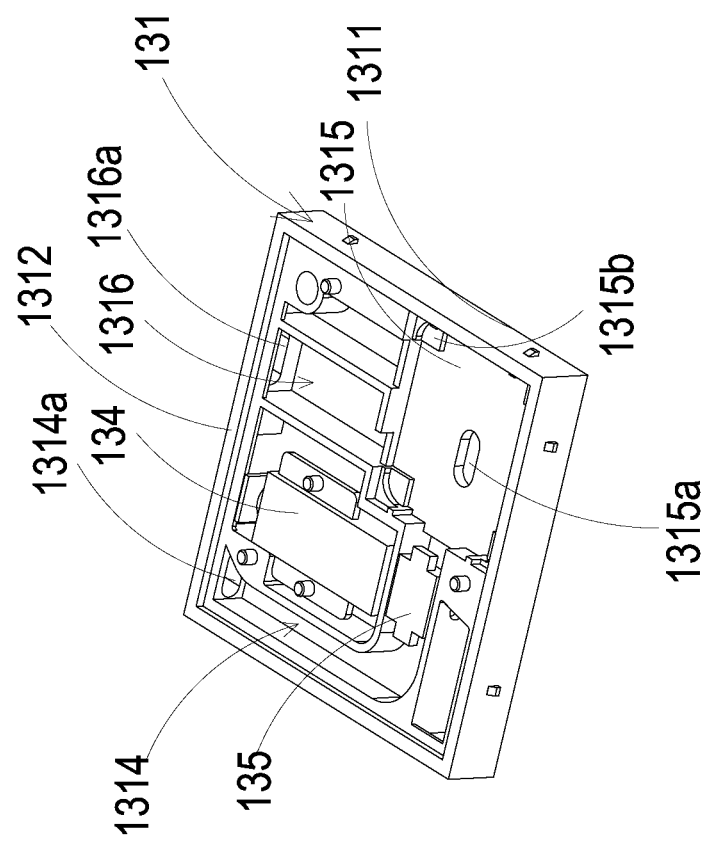
FIG. 4 is a schematic view illustrating a laser component and a sensor received within the base of the gas detection device in FIG. 2C.

Please refer to FIG. 2C and FIG. 4. In the embodiment, the laser component 134 and the particulate sensor 135 are disposed on the driving circuit board 133 and located within the base 131. In order to clearly describe and illustrate the positions of the laser component 134 and the particulate sensor 135 in the base 131, the driving circuit board 133 is specifically omitted in FIG. 4. The laser component 134 is accommodated in the laser loading region 1313 of the base 131, and the particulate sensor 135 is accommodated in the gas-inlet groove 1314 of the base 131 and is aligned to the laser component 134. In addition, the laser component 134 is spatially corresponding to the transparent window 1314b, therefore a light beam emitted by the laser component 134 passes through the transparent window 1314b and is irradiated into the gas-inlet groove 1314. A light beam path emitted from the laser component 134 passes through the transparent window 1314b and extends in an orthogonal direction perpendicular to the gas-inlet groove 1314.

In the embodiment, a projecting light beam emitted from the laser component 134 passes through the transparent window 1314b and enters the gas-inlet groove 1314 to irradiate the suspended particles contained in the gas passing through the gas-inlet groove 1314. When the suspended particles contained in the gas are irradiated and generate scattered light spots, the scattered light spots are received and calculated by the particulate sensor 135 for obtaining related information about the sizes and the concentration of the suspended particles contained in the gas. In the embodiment, the particulate sensor 135 is a PM2.5 sensor.

In the embodiment, the at least one sensor 135 of the gas detection module 13 includes a volatile organic compound sensor for detecting and obtaining the gas information of $CO_2$ or TVOC. The at least one sensor 135 of the gas detection module 13 includes a formaldehyde sensor for detecting and obtaining the gas information of formaldehyde. The at least one sensor 135 of the gas detection module 13 includes a particulate sensor for detecting and obtaining the gas information of PM1, PM2.5 or PM10. The at least one sensor 135 of the gas detection module 13 includes a pathogenic bacteria sensor for detecting and obtaining the gas information of bacteria or pathogenic bacteria.

The gas detection module 13 of the present disclosure not only detects the suspended particles in the gas, but also detects the characteristics of the introduced gas. Preferably but not exclusively, the characteristics of the introduced gas can be detected is selected from the group consisting of formaldehyde, ammonia, carbon monoxide, carbon dioxide, oxygen, ozone, bacteria, pathogenic bacteria, virus and a combination thereof. In the embodiment, the gas detection module 13 further includes a first volatile-organic-compound sensor 137a. The first volatile-organic-compound sensor 137a positioned and disposed on the driving circuit board 133 is electrically connected to the driving circuit board 133, and is accommodated in the gas-outlet groove 1316, so as to detect the gas flowing through the outlet path of the gas-outlet groove 1316. Thus, the concentration or the characteristics of volatile organic compounds contained in the gas in the outlet path can be detected. Alternatively, in an embodiment, the gas detection module 13 further includes a second volatile-organic-compound sensor 137b. The second volatile-organic-compound sensor 137b positioned and disposed on the driving circuit board 133 is electrically connected to the driving circuit board 133 and is accommodated in the light trapping region 1317. Thus, the concentration or the characteristics of volatile organic compounds contained in the gas flowing through the inlet path of the gas-inlet groove 1314 and transporting into the light trapping region 1317 through the transparent window 1314b is detected.

Figure 5A:
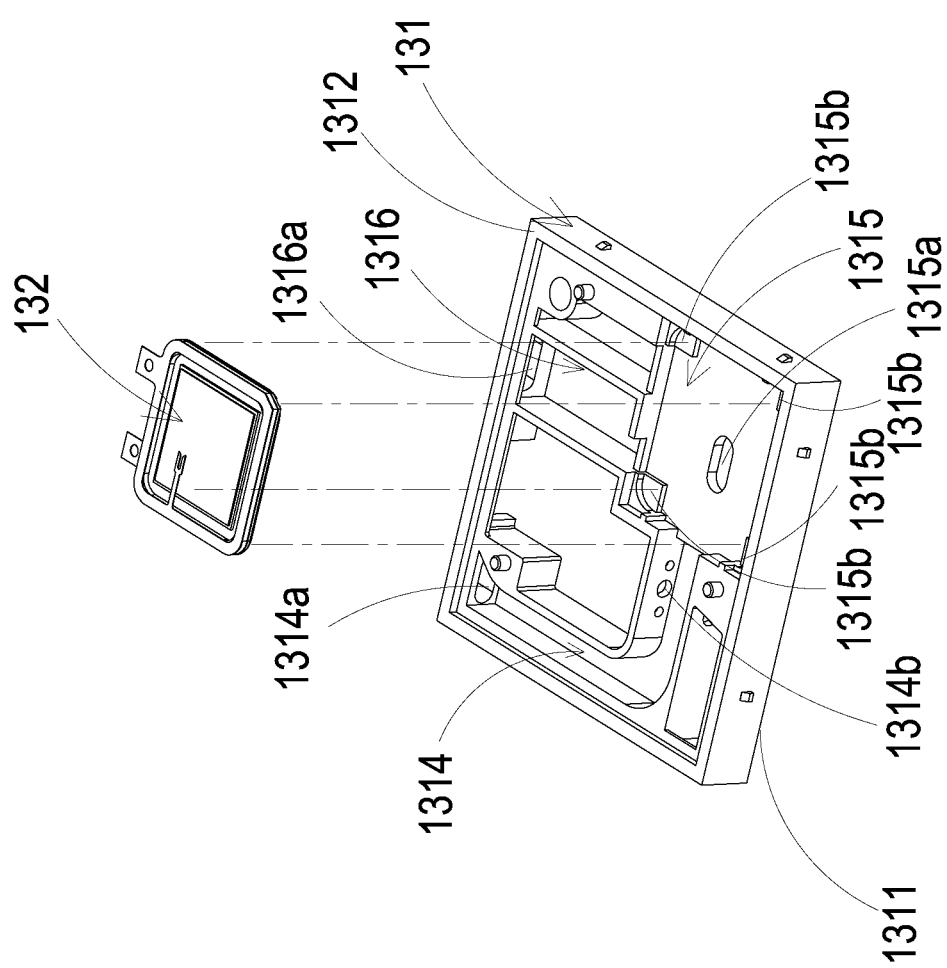
FIG. 5A is a schematic exploded view illustrating the combination of the piezoelectric actuator and the base of the gas detection main part in FIG. 2C.
Figure 5B:
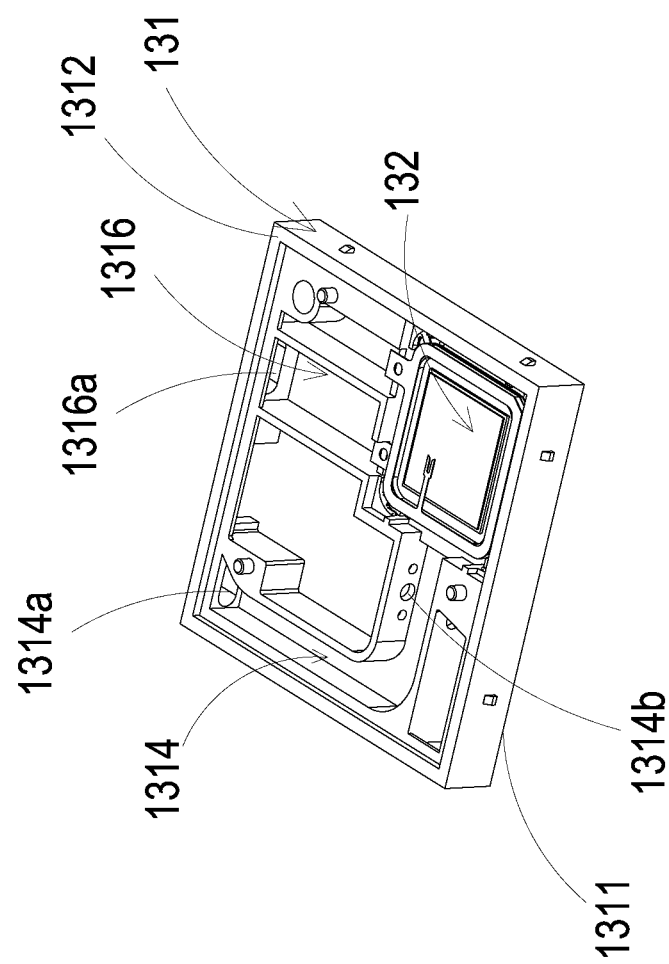
FIG. 5B is a schematic perspective view illustrating the combination of the piezoelectric actuator and the base of the gas detection main part in FIG. 2C.

Please refer to FIG. 5A and FIG. 5B. The piezoelectric actuator 132 is accommodated in the gas-guiding-component loading region 1315 of the base 131. Preferably but not exclusively, the gas-guiding-component loading region 1315 is square-shaped and includes four positioning protrusions 1315b disposed at four corners of the gas-guiding-component loading region 1315, respectively. The piezoelectric actuator 132 is disposed in the gas-guiding-component loading region 1315 through the four positioning protrusions 1315b. In addition, as shown in FIGS. 3A, 3B, 8B and 8C, the gas-guiding-component loading region 1315 is in communication with the gas-inlet groove 1314. When the piezoelectric actuator 132 is enabled, the gas in the gas-inlet groove 1314 is inhaled by the piezoelectric actuator 132, so that the gas flows into the piezoelectric actuator 132, and is transported into the gas-outlet groove 1316 through the ventilation hole 1315a of the gas-guiding-component loading region 1315.

Figure 8A:
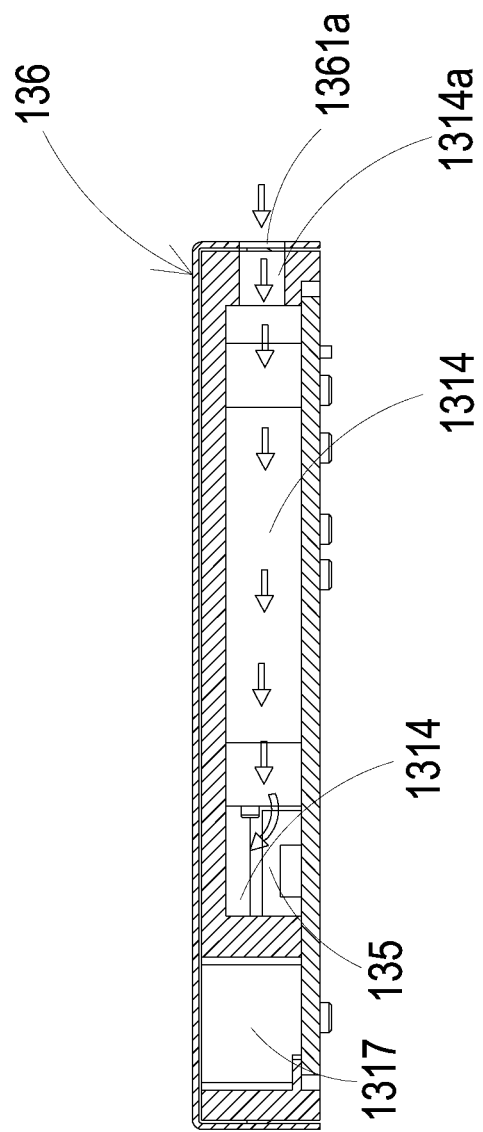
FIGS. 8A to 8C schematically illustrate gas flowing paths of the gas detection device in FIG. 2B from different angles.
Figure 8B:
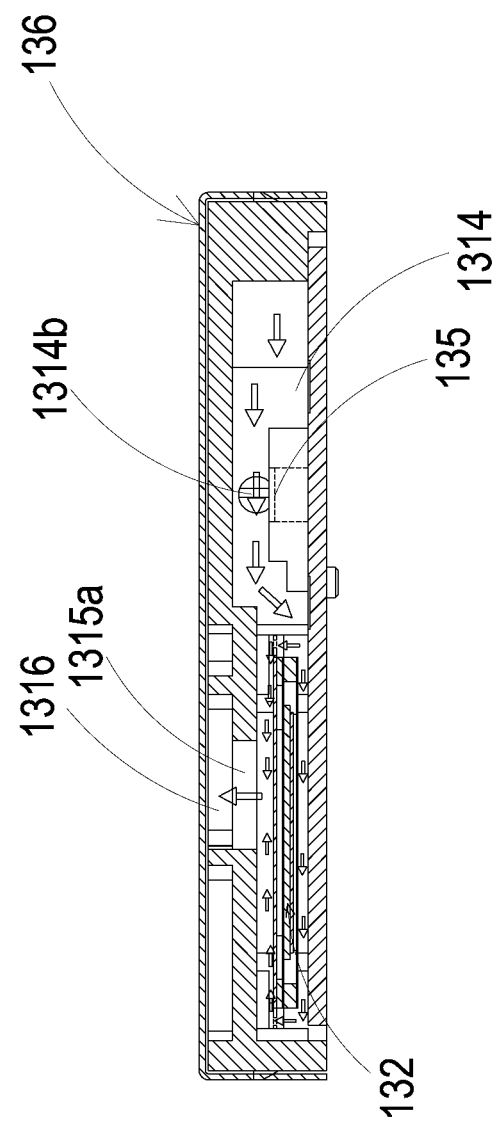
Figure 8C:
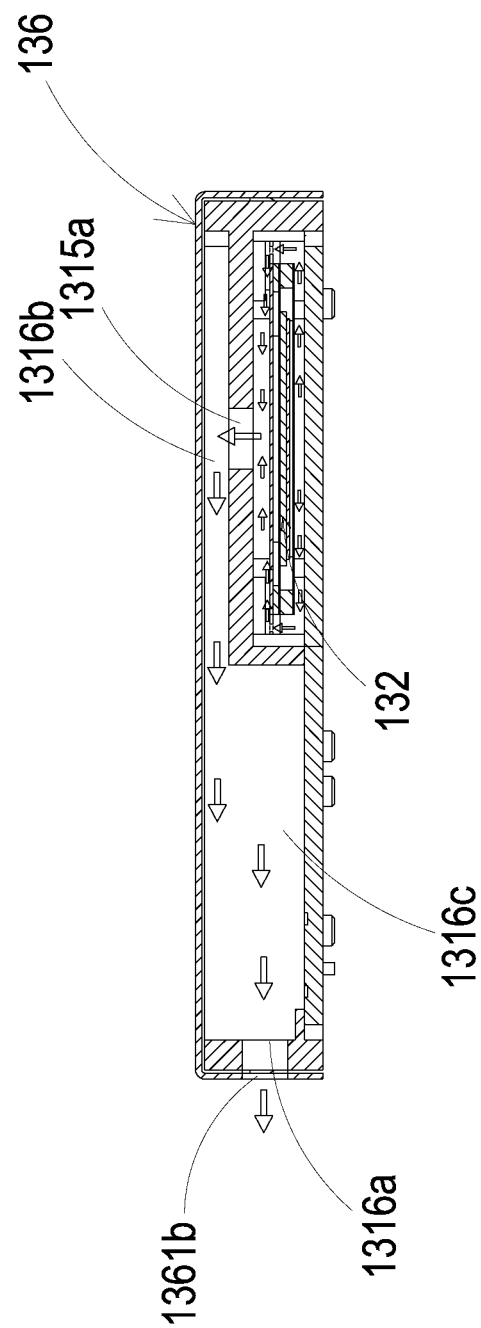

Please refer to FIGS. 2B and 2C. In the embodiment, the driving circuit board 133 covers and is attached to the second surface 1312 of the base 131, and the laser component 134 is positioned and disposed on the driving circuit board 133, and is electrically connected to the driving circuit board 133. The particulate sensor 135 is positioned and disposed on the driving circuit board 133, and is electrically connected to the driving circuit board 133. As shown in FIG. 2B, when the outer cover 136 covers the base 131, the inlet opening 1361a is spatially corresponding to the gas-inlet 1314a of the base 131 (as shown in FIG. 8A), and the outlet opening 1361b is spatially corresponding to the gas-outlet 1316a of the base 131 (as shown in FIG. 8C).

Figure 6A:
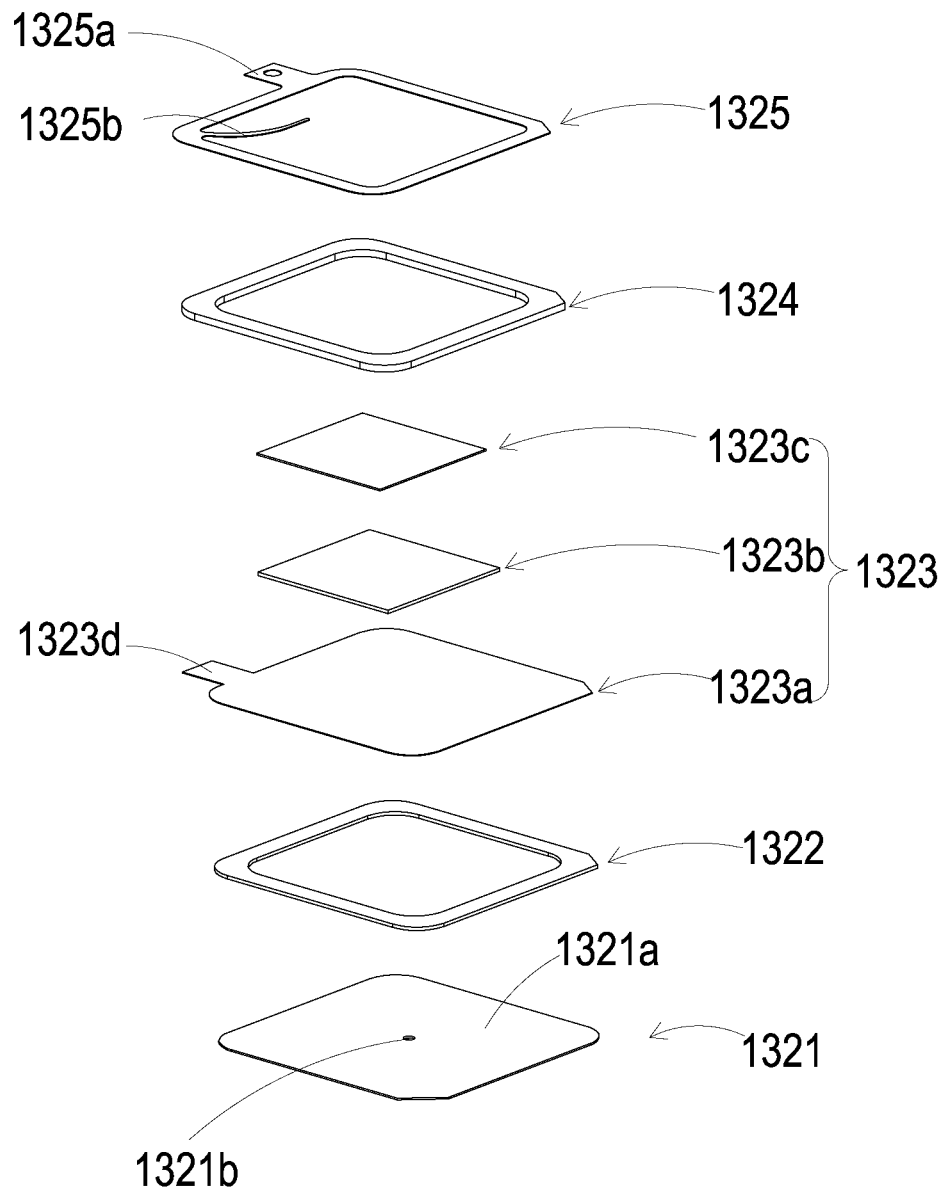
FIG. 6A is a schematic exploded front view illustrating the piezoelectric actuator of the gas detection device in FIG. 2C.
Figure 6B:
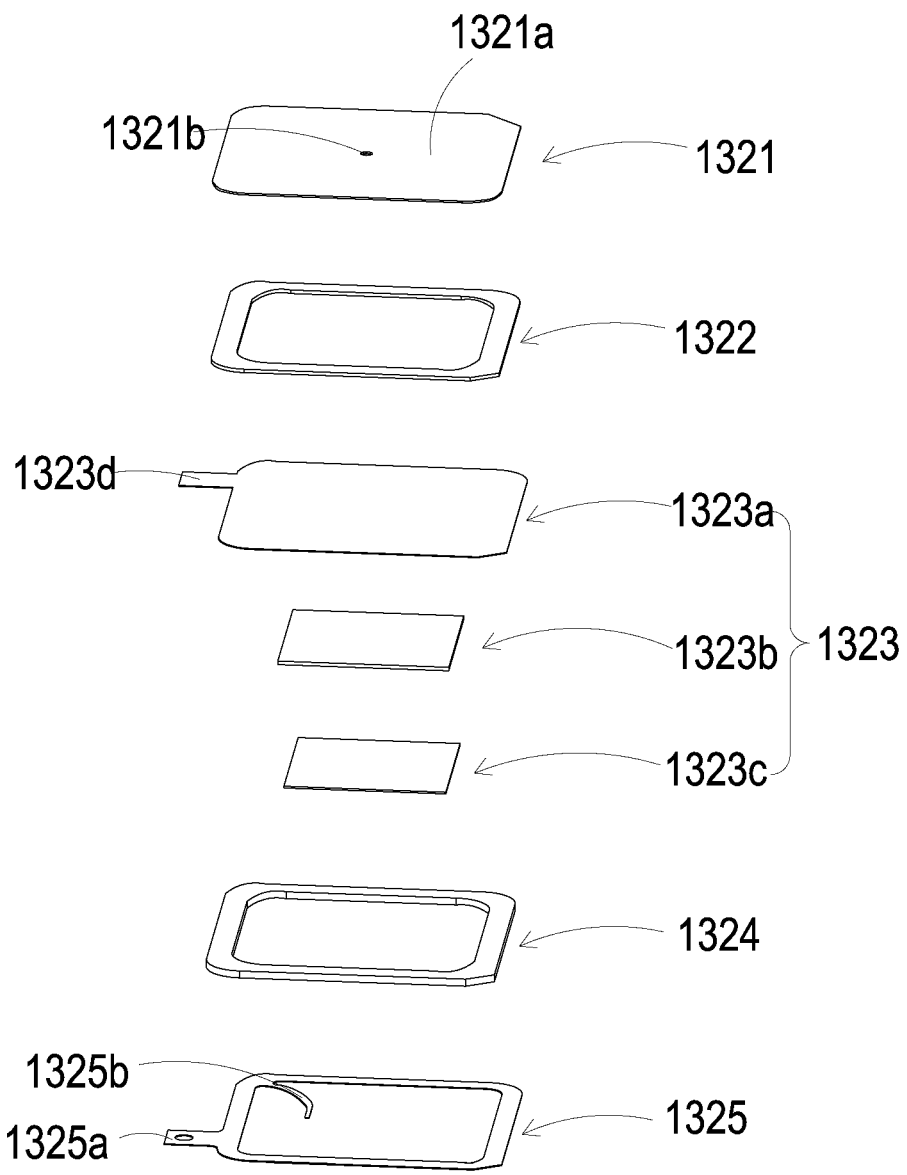
FIG. 6B is a schematic exploded rear view illustrating the piezoelectric actuator of the gas detection device in FIG. 2C.

Please refer to FIGS. 6A and 6B. In the embodiment, the piezoelectric actuator 132 includes a gas-injection plate 1321, a chamber frame 1322, an actuator element 1323, an insulation frame 1324 and a conductive frame 1325. In the embodiment, the gas-injection plate 1321 is made by a flexible material and includes a suspension plate 1321a and a hollow aperture 1321b. The suspension plate 1321a is a sheet structure and is permitted to undergo a bending deformation. Preferably but not exclusively, the shape and the size of the suspension plate 1321a are accommodated in the inner edge of the gas-guiding-component loading region 1315, but not limited thereto. The shape of the suspension plate 1321a is selected from the group consisting of a square, a circle, an ellipse, a triangle and a polygon. The hollow aperture 1321b passes through a center of the suspension plate 1321a, so as to allow the gas to flow therethrough.

Figure 7A:
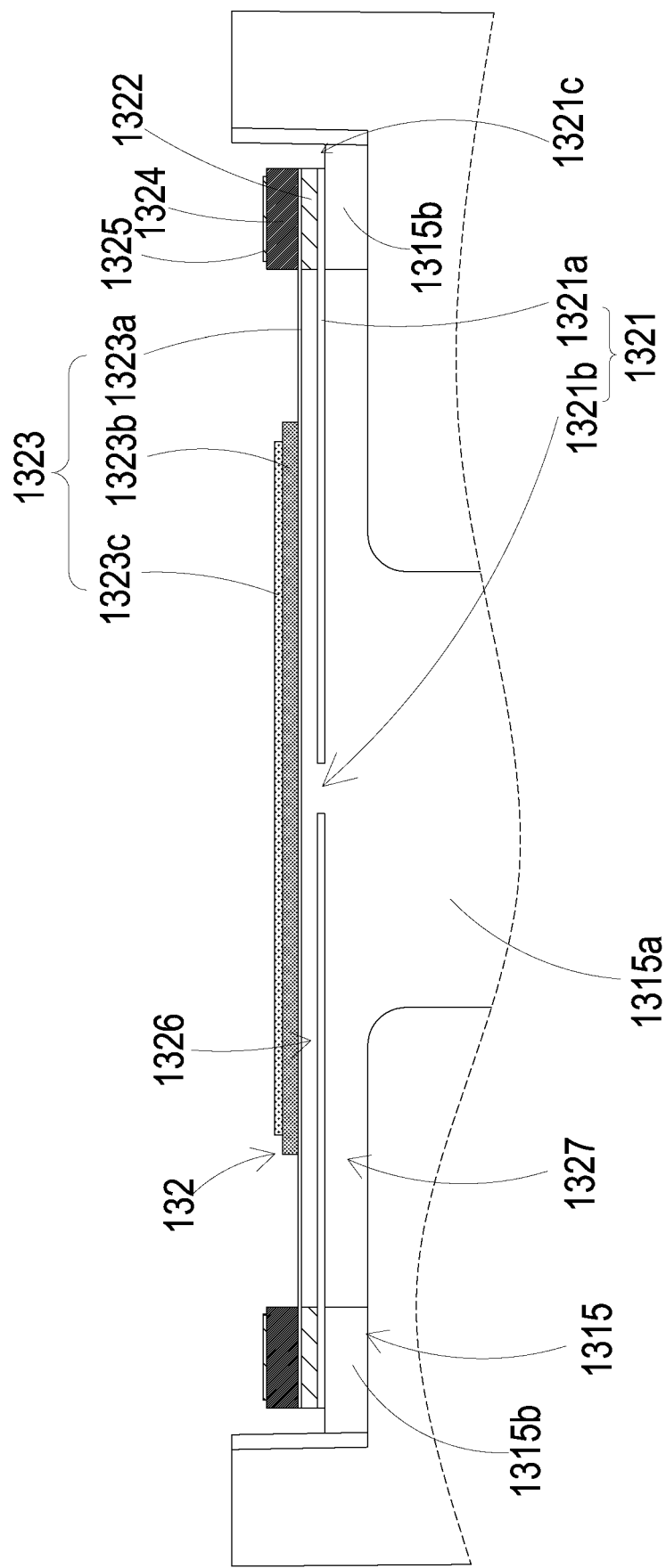
FIG. 7A is a schematic cross-sectional view illustrating the piezoelectric actuator of the gas detection device in FIG. 6A accommodated in the gas-guiding-component loading region according to the embodiment of the present disclosure.

Please refer to FIG. 6A, FIG. 6B and FIG. 7A. In the embodiment, the chamber frame 1322 is carried and stacked on the gas-injection plate 1321. In addition, the shape of the chamber frame 1322 is corresponding to the gas-injection plate 1321. The actuator element 1323 is carried and stacked on the chamber frame 1322. A resonance chamber 1326 is collaboratively defined by the actuator element 1323, the chamber frame 1322 and the suspension plate 1321a and is formed between the actuator element 1323, the chamber frame 1322 and the suspension plate 1321a. The insulation frame 1324 is carried and stacked on the actuator element 1323 and the appearance of the insulation frame 1324 is similar to that of the chamber frame 1322. The conductive frame 1325 is carried and stacked on the insulation frame 1324, and the appearance of the conductive frame 1325 is similar to that of the insulation frame 1324. In addition, the conductive frame 1325 includes a conducting pin 1325a and a conducting electrode 1325b. The conducting pin 1325a is extended outwardly from an outer edge of the conductive frame 1325, and the conducting electrode 1325b is extended inwardly from an inner edge of the conductive frame 1325. Moreover, the actuator element 1323 further includes a piezoelectric carrying plate 1323a, an adjusting resonance plate 1323b and a piezoelectric plate 1323c. The piezoelectric carrying plate 1323a is carried and stacked on the chamber frame 1322. The adjusting resonance plate 1323b is carried and stacked on the piezoelectric carrying plate 1323a. The piezoelectric plate 1323c is carried and stacked on the adjusting resonance plate 1323b. The adjusting resonance plate 1323b and the piezoelectric plate 1323c are accommodated in the insulation frame 1324. The conducting electrode 1325b of the conductive frame 1325 is electrically connected to the piezoelectric plate 1323c. In the embodiment, the piezoelectric carrying plate 1323a and the adjusting resonance plate 1323b are made by a conductive material. The piezoelectric carrying plate 1323a includes a piezoelectric pin 1323d. The piezoelectric pin 1323d and the conducting pin 1325a are electrically connected to a driving circuit (not shown) of the driving circuit board 133, so as to receive a driving signal, such as a driving frequency and a driving voltage. Through this structure, a circuit is formed by the piezoelectric pin 1323d, the piezoelectric carrying plate 1323a, the adjusting resonance plate 1323b, the piezoelectric plate 1323c, the conducting electrode 1325b, the conductive frame 1325 and the conducting pin 1325a for transmitting the driving signal. Moreover, the insulation frame 1324 is insulated between the conductive frame 1325 and the actuator element 1323, so as to avoid the occurrence of a short circuit. Thereby, the driving signal is transmitted to the piezoelectric plate 1323c. After receiving the driving signal such as the driving frequency and the driving voltage, the piezoelectric plate 1323c deforms due to the piezoelectric effect, and the piezoelectric carrying plate 1323a and the adjusting resonance plate 1323b are further driven to generate the bending deformation in the reciprocating manner.

As described above, the adjusting resonance plate 1323b is located between the piezoelectric plate 1323c and the piezoelectric carrying plate 1323a and served as a cushion between the piezoelectric plate 1323c and the piezoelectric carrying plate 1323a. Thereby, the vibration frequency of the piezoelectric carrying plate 1323a is adjustable. Basically, the thickness of the adjusting resonance plate 1323b is greater than the thickness of the piezoelectric carrying plate 1323a, and the thickness of the adjusting resonance plate 1323b is adjustable, thereby the vibration frequency of the actuator element 1323 can be adjusted accordingly.

Please refer to FIG. 6A, FIG. 6B and FIG. 7A. In the embodiment, the gas-injection plate 1321, the chamber frame 1322, the actuator element 1323, the insulation frame 1324 and the conductive frame 1325 are stacked and positioned in the gas-guiding-component loading region 1315 sequentially, so that the piezoelectric actuator 132 is supported and positioned in the gas-guiding-component loading region 1315. The bottom of the gas-injection plate 1321 is fixed on the four positioning protrusions 1315b of the gas-guiding-component loading region 1315 for supporting and positioning, so that a plurality of vacant spaces 1321c are defined between the suspension plate 1321a of the gas-injection plate 1321 and an inner edge of the gas-guiding-component loading region 1315 for gas flowing therethrough.

Please refer to FIG. 7A. A flowing chamber 1327 is formed between the gas-injection plate 1321 and the bottom surface of the gas-guiding-component loading region 1315. The flowing chamber 1327 is in communication with the resonance chamber 1326 between the actuator element 1323, the chamber frame 1322 and the suspension plate 1321a through the hollow aperture 1321b of the gas-injection plate 1321. By controlling the vibration frequency of the gas in the resonance chamber 1326 to be close to the vibration frequency of the suspension plate 1321a, the Helmholtz resonance effect is generated between the resonance chamber 1326 and the suspension plate 1321a, so as to improve the efficiency of gas transportation.

Figure 7B:
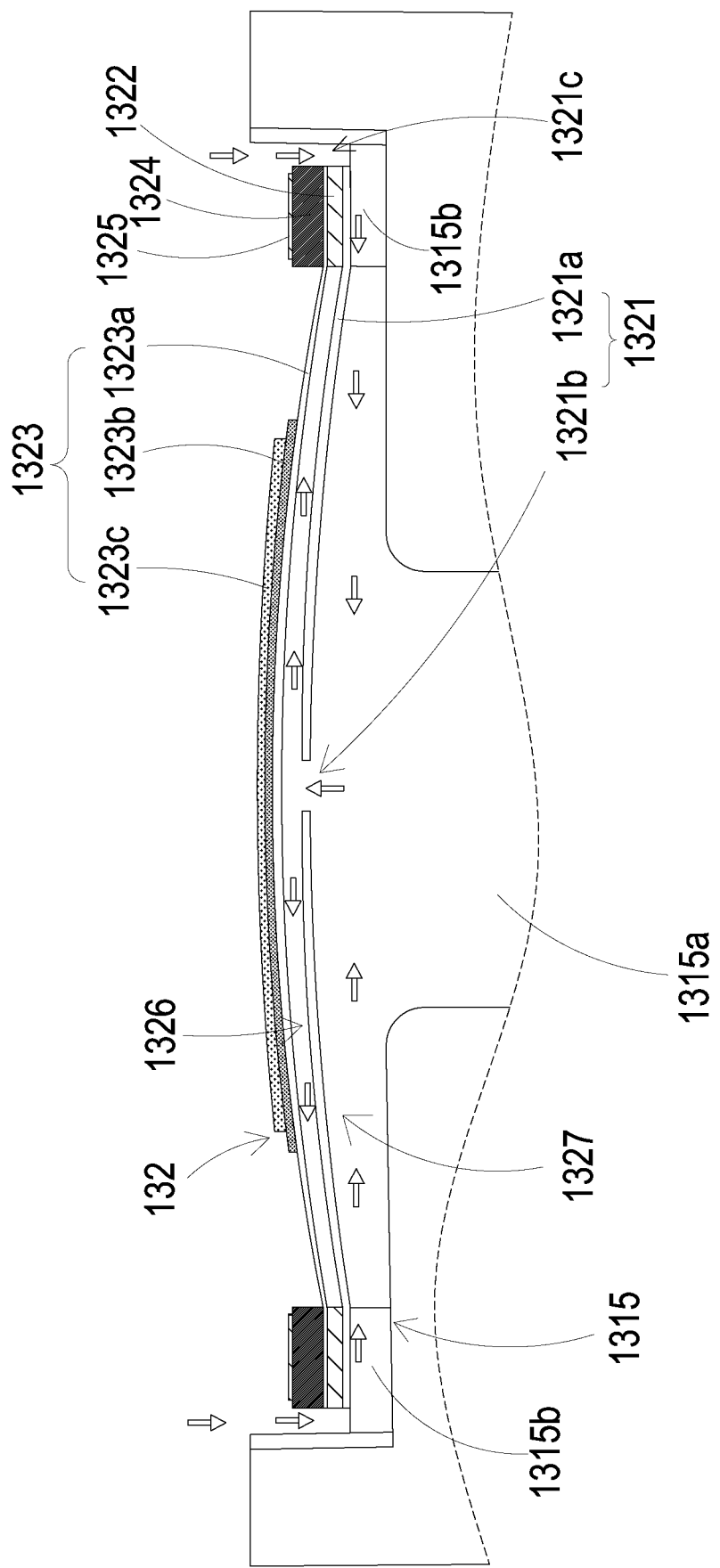
FIGS. 7B and 7C schematically illustrate the operation steps of the piezoelectric actuator of FIG. 7A.
Figure 7C:
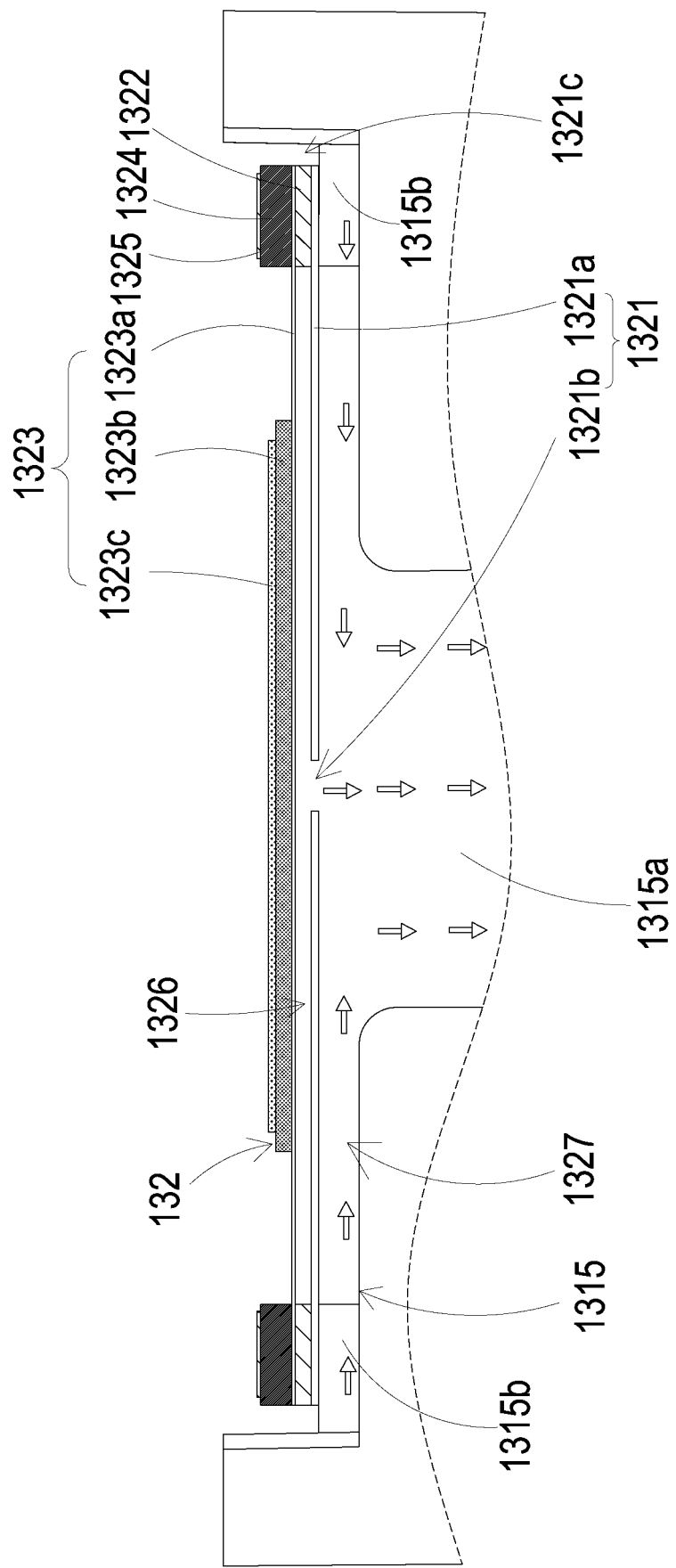

Please refer to FIG. 7B. When the piezoelectric plate 1323c is moved away from the bottom surface of the gas-guiding-component loading region 1315, the suspension plate 1321a of the gas-injection plate 1321 is driven to move away from the bottom surface of the gas-guiding-component loading region 1315 by the piezoelectric plate 1323c. In that, the volume of the flowing chamber 1327 is expanded rapidly, the internal pressure of the flowing chamber 1327 is decreased to form a negative pressure, and the gas outside the piezoelectric actuator 132 is inhaled through the vacant spaces 1321c and enters the resonance chamber 1326 through the hollow aperture 1321b. Consequently, the pressure in the resonance chamber 1326 is increased to generate a pressure gradient. Further as shown in FIG. 7C, when the suspension plate 1321*a* of the gas-injection plate 1321 is driven by the piezoelectric plate 1323*c* to move toward the bottom surface of the gas-guiding-component loading region 1315, the gas in the resonance chamber 1326 is discharged out rapidly through the hollow aperture 1321*b*, and the gas in the flowing chamber 1327 is compressed, thereby the converged gas is quickly and massively ejected out of the flowing chamber 1327 under the condition close to an ideal gas state of the Benulli's law, and transported to the ventilation hole 1315*a* of the gas-guiding-component loading region 1315. By repeating the above operation steps shown in FIG. 7B and FIG. 7C, the piezoelectric plate 1323*c* is driven to generate the bending deformation in a reciprocating manner. According to the principle of inertia, since the gas pressure inside the resonance chamber 1326 is lower than the equilibrium gas pressure after the converged gas is ejected out, the gas is introduced into the resonance chamber 1326 again. Moreover, the vibration frequency of the gas in the resonance chamber 1326 is controlled to be close to the vibration frequency of the piezoelectric plate 1323*c*, so as to generate the Helmholtz resonance effect to achieve the gas transportation at high speed and in large quantities.

Furthermore, as shown in FIG. 8A, the gas is inhaled through the inlet opening 1361*a* of the outer cover 136, flows into the gas-inlet groove 1314 of the base 131 through the gas-inlet 1314*a*, and is transported to the position of the particulate sensor 135. Further as shown in FIG. 8B, the piezoelectric actuator 132 is enabled continuously to inhale the gas into the inlet path, and facilitate the gas to be introduced rapidly, flow stably, and be transported above the particulate sensor 135. At this time, a projecting light beam emitted from the laser component 134 passes through the transparent window 1314*b* to irritate the suspended particles contained in the gas flowing above the particulate sensor 135 in the gas-inlet groove 1314. When the suspended particles contained in the gas are irradiated and generate scattered light spots, the scattered light spots are received and calculated by the particulate sensor 135 for obtaining related information about the sizes and the concentration of the suspended particles contained in the gas. Moreover, the gas above the particulate sensor 135 is continuously driven and transported by the piezoelectric actuator 132, flows into the ventilation hole 1315*a* of the gas-guiding-component loading region 1315, and is transported to the first section 1316*b* of the gas-outlet groove 1316. As shown in FIG. 8C, after the gas flows into the first section 1316*b* of the gas-outlet groove 1316, the gas is continuously transported into the first section 1316*b* by the piezoelectric actuator 132, and the gas in the first section 1316*b* is pushed to the second section 1316*c*. Finally, the gas is discharged out through the gas-outlet 1316*a* and the outlet opening 1361*b*.

Figure 9:
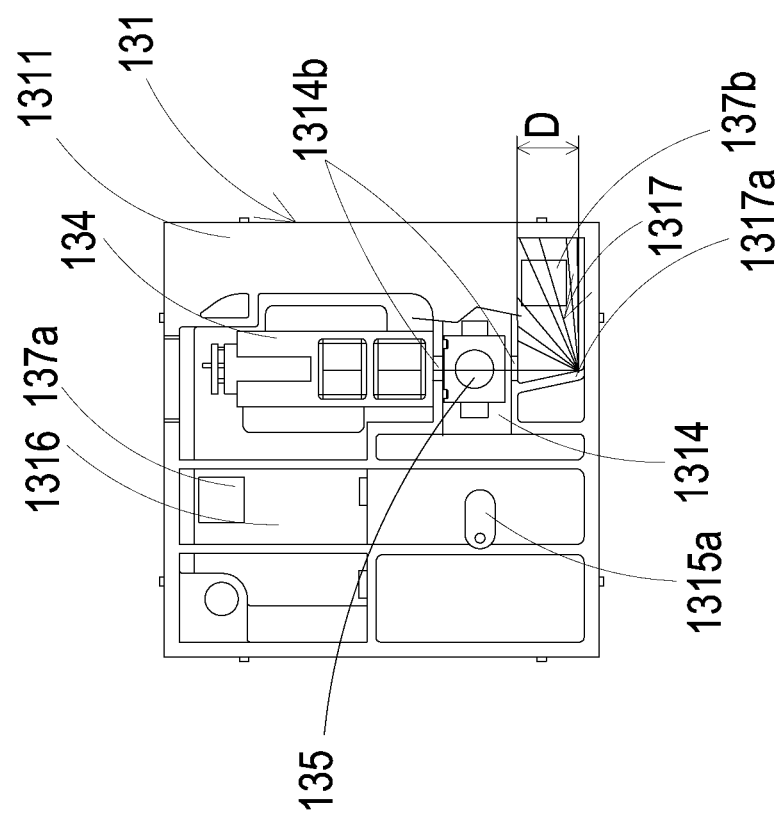
FIG. 9 schematically illustrates a light beam path emitted from the laser component of the gas detection device in FIG. 2C.

As shown in FIG. 9, the base 131 further includes a light trapping region 1317. The light trapping region 1317 is hollowed out from the first surface 1311 to the second surface 1312 and is spatially corresponding to the laser loading region 1313. In the embodiment, the light beam emitted by the laser component 134 is projected into the light trapping region 1317 through the transparent window 1314*b*. The light trapping region 1317 includes a light trapping structure 1317*a* having an oblique cone surface. The light trapping structure 1317*a* is spatially corresponding to the light beam path emitted from the laser component 134. In addition, the projecting light beam emitted from the laser component 134 is reflected into the light trapping region 1317 through the oblique cone surface of the light trapping structure 1317*a*, so as to prevent the projecting light beam from reflecting back to the position of the particulate sensor 135. In the embodiment, a light trapping distance D is maintained between the transparent window 1314*b* and a position where the light trapping structure 1317*a* receives the projecting light beam, so as to avoid the projecting light beam projecting on the light trapping structure 1317*a* from reflecting back to the position of the particulate sensor 135 directly due to excessive stray light generated after reflection, and result in distortion of detection accuracy.

Please refer to FIG. 2C and FIG. 9. The gas detection module 13 of the present disclosure not only detects the suspended particles in the gas, but also detects the characteristics of the introduced gas. Preferably but not exclusively, the characteristics of the introduced gas can be detected is selected from the group consisting of formaldehyde, ammonia, carbon monoxide, carbon dioxide, oxygen, ozone, bacteria, pathogenic bacteria, virus and a combination thereof. In the embodiment, the gas detection module 13 further includes a first volatile-organic-compound sensor 137*a*. The first volatile-organic-compound sensor 137*a* positioned and disposed on the driving circuit board 133 is electrically connected to the driving circuit board 133, and is accommodated in the gas-outlet groove 1316, so as to detect the gas flowing through the outlet path of the gas-outlet groove 1316. Thus, the concentration or the characteristics of volatile organic compounds contained in the gas in the outlet path can be detected. Alternatively, in an embodiment, the gas detection module 13 further includes a second volatile-organic-compound sensor 137*b*. The second volatile-organic-compound sensor 137*b* positioned and disposed on the driving circuit board 133 is electrically connected to the driving circuit board 133 and is accommodated in the light trapping region 1317. Thus, the concentration or the characteristics of volatile organic compounds contained in the gas flowing through the inlet path of the gas-inlet groove 1314 and transporting into the light trapping region 1317 through the transparent window 1314*b* is detected.

Figure 10A:
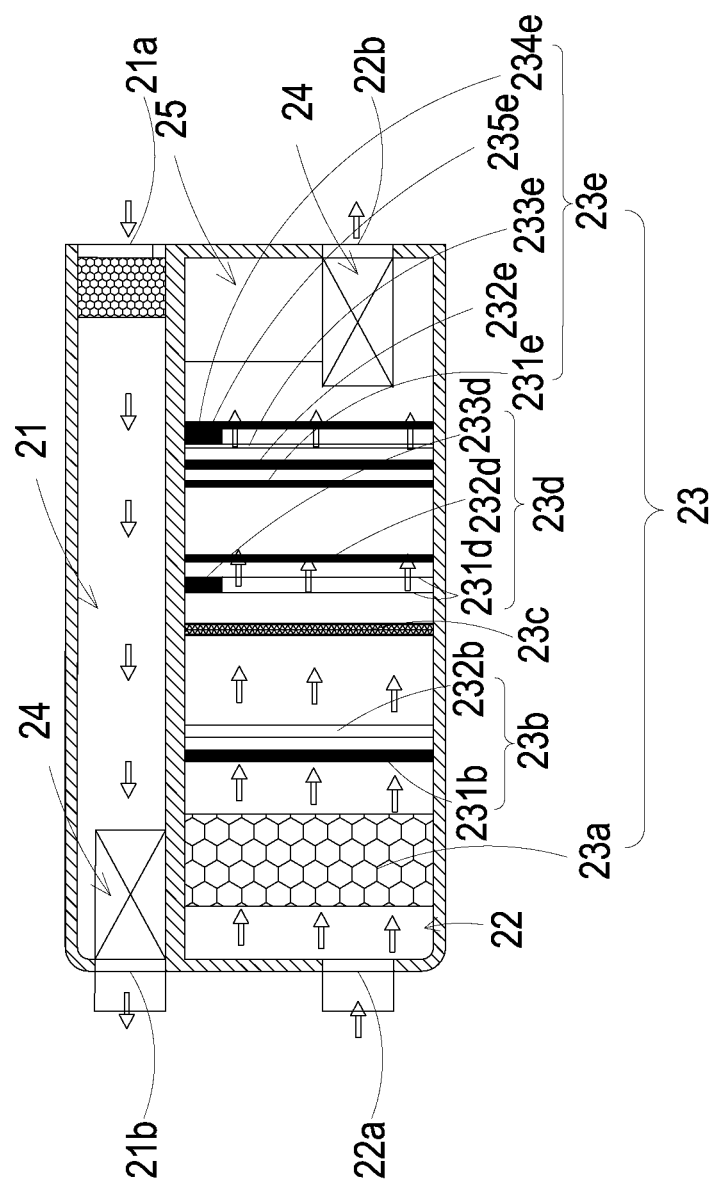
FIGS. 10A to 10C are cross-sectional views illustrating the gas exchangers for implementing the method of preventing and handling indoor air pollution according to the embodiment of the present disclosure.

Please refer to FIG. 1A and FIG. 10A. The gas exchanger 2 includes a gas-inlet channel 22, a gas-outlet channel 21, at least one gas guider 24, a purification unit 23 and a remote-control driving device 25. The remote-control driving device 25 is disposed inside the gas exchanger 2 and adjacent to the gas guider 24. When the remote-control driving device 25 receives the air pollutant information that the portable gas detection device 1 detects in the indoor space A, the gas exchanger 2 receives a control signal from the portable gas detection device 1, so that the gas is inhaled from the outdoor into the gas exchanger 2 by the gas guider 24, transported through the gas inlet channel 22, purified and filtered by the purification unit 23, and then introduced into the indoor space A, and the air pollutant in the indoor space A is exported out to the outdoors through the gas-outlet channel 21. The purification unit 23 is a high efficiency particulate air filter screen 23*a*. The high efficiency particulate air filter screen 23*a* is coated with a cleansing factor containing chlorine dioxide to inhibit viruses and bacteria in the gas. The high efficiency particulate air filter screen 23*a* is coated with an herbal protective layer extracted from ginkgo and Japanese rhus chinensis to form an herbal protective anti-allergic filter, so as to resist allergy effectively and destroy a surface protein of influenza virus. The high efficiency particulate air filter screen 23*a* is coated with a silver ion to inhibit viruses and bacteria. The purification unit 23 is at least one selected from the group consisting of a photo-catalyst unit 23*b*, a photo-plasma unit 23*c*, a negative ionizer 23*d* and a plasma ion unit 23*e*, which is combined with the high efficiency particulate air filter screen 23*a*.

Please refer to FIG. 10A, again. In the embodiment, the gas exchanger 2 includes a gas-inlet channel 22, a gas-outlet channel 21, at least one gas guider 24, a purification unit 23 and a remote-control driving device 25. In an embodiment, the gas-outlet channel 21 includes a gas-outlet-channel inlet 21a and a gas-outlet-channel outlet 21b disposed at two ends thereof, respectively. The gas-inlet channel 22 includes a gas-inlet-channel inlet 22a and a gas-inlet-channel outlet 22b disposed at two ends thereof, respectively. The purification unit 23 is disposed within the gas-inlet channel 22 for filtering and purifying the introduced gas. The gas guider 24 is disposed within the gas-inlet channel 22 and located at one side of the purification unit 23, so that the gas is introduced from the gas-inlet-channel inlet 22a and transported into the purification unit 23 to obtain a purified gas. Finally, the gas is discharged from the gas-inlet-channel outlet 22b and introduced into the indoor space A. Therefore, the enablement or disablement of the gas guider 24 is control by the gas detection module 13. When the gas guider 24 is enabled, the outdoor gas is inhaled from outdoor through the gas-inlet-channel inlet 22a into the gas-inlet channel 22, transported into the purification unit 23 for filtering and purifying, and finally discharged out through the gas-inlet-channel outlet 22b into the indoor space A. In that, the filtered and purified gas is provided to the indoor space A, and the air pollutant in the gas in the indoor space A is exchanged and exported through the gas-outlet channel 21 to the outdoor environment.

Figure 10B:
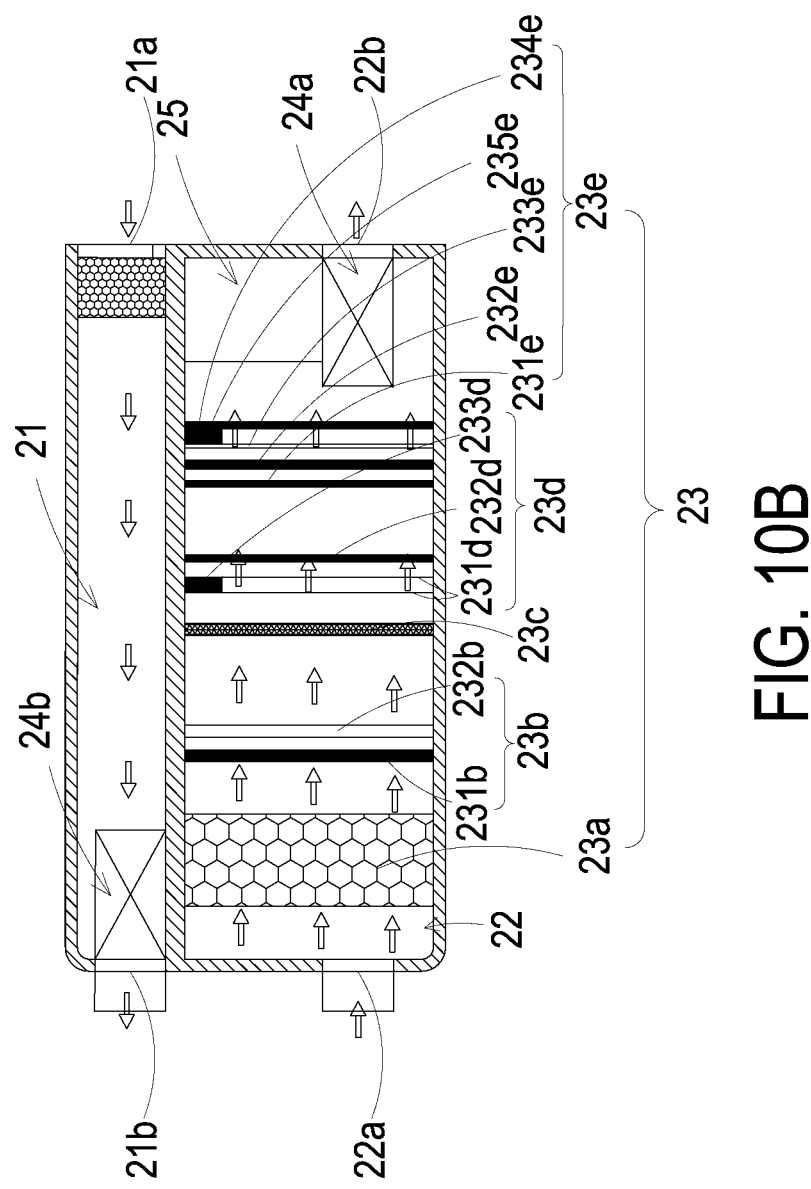

Please refer to FIG. 10B, again. In the embodiment, the gas guider 24 includes a gas-inlet guider 24a and a gas-outlet guider 24b. The purification unit 23 is disposed within the gas-inlet channel 22 for filtering and purifying. The gas-inlet guider 24a is disposed within the gas-inlet channel 22 and located at one side of the purification unit 23, and the gas-outlet guider 24b is disposed within the gas-outlet channel 21. The enablement or disablement of the gas-inlet guider 24a and the gas-outlet guider 24b is controlled by the gas detection module 13. When the gas-inlet guider 24a and the gas-outlet guider 24b are enabled, the outdoor gas is inhaled through the gas-inlet-channel inlet 22a into the gas-inlet channel 22, transported into the purification unit 23 for filtering and purifying, and finally discharged out through the gas-inlet-channel outlet 22b into the indoor space A. In that, the filtered and purified gas is provided to the indoor space A, and the air pollutant in the gas within the indoor space A is introduced through the gas-outlet-channel inlet 21a into the gas-outlet channel 21, exchanged and discharged through the gas-outlet-channel outlet 21b to the outdoor environment.

In the embodiment, the remote-control driving device 25 is configured to receive a control signal to enable the gas exchanger 2. That is, when the air pollutant in the indoor space A is detected by the portable gas detection device 1, the remote-control signal is transmitted from the portable gas detection device 1 and received by the remote-control driving device 25, so as to allow the portable gas detection device 1 to remotely control an actuation of the gas exchanger 2 and enable the gas-inlet guider 24a and the gas-outlet guider 24b of the gas exchanger 2, thereby the gas is inhaled from the outdoor environment into the gas inlet channel 22, transported through the purification unit 23 for filtering and purifying, and then introduced into the indoor space A, and the air pollutant in the indoor space A is introduced by the gas-outlet guider 24b and exchanged and exported out to the outdoor environment through the gas-outlet channel 21.

Figure 10C:
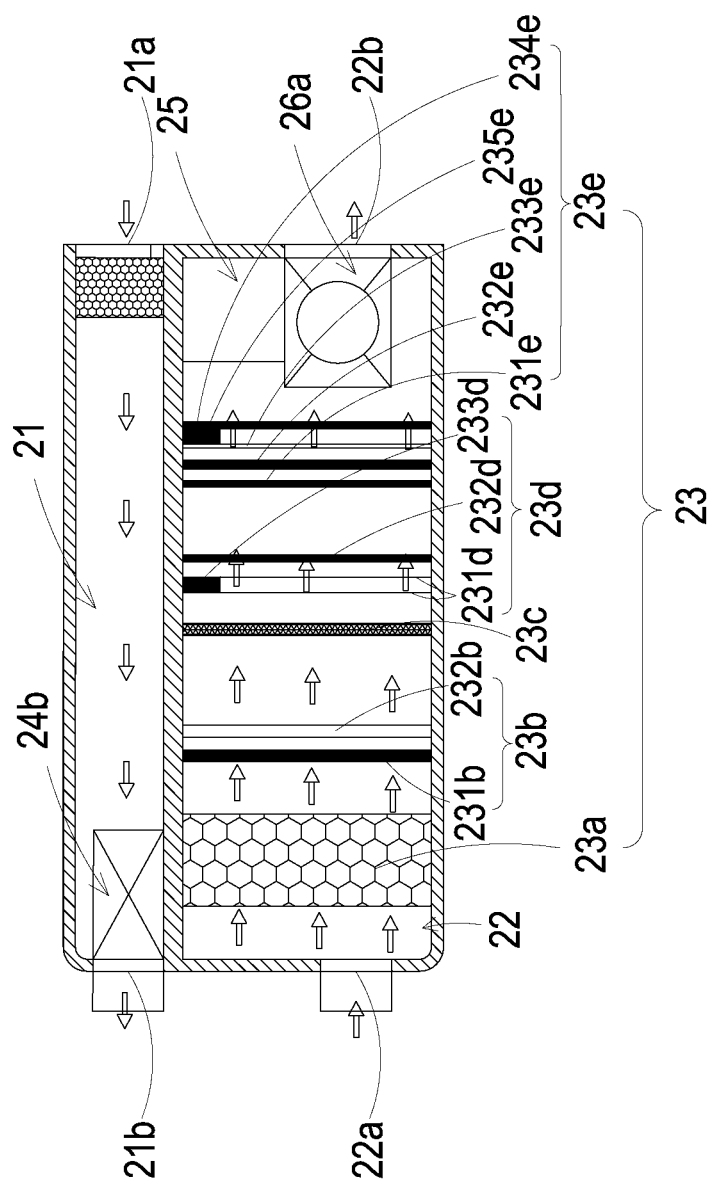

Please refer to FIG. 10C. In the embodiment, the gas exchanger 2 includes a gas-inlet channel 22, a gas-outlet channel 21, a purification unit 23, a remote-control driving device 25 and an air-conditioner 26a. When the portable gas detection device 1 detects the air pollutant in the indoor space A, the remote-control driving device 25 receives a control signal therefrom, so that the gas is inhaled from the outdoor environment into the gas exchanger 2 through the air-conditioner 26a, transported through the gas inlet channel 22, purified and filtered by the purification unit 23, adjusted the temperature and humidity of the gas by the air-conditioner 26a, and then introduced into the indoor space A, and the air pollutant in the indoor space A is exported out to the outdoor environment through the gas-outlet channel 21. In the embodiment, the air-conditioner 26a can be enabled or disabled by the remote-control driving device 25. In that, the temperature and humidity of the gas in the indoor space A is controlled by the air-conditioner 26a, so as to reach a suitable temperature and humidity set in the indoor space A.

Notably, in an embodiment, the air-conditioner 26a can increase the temperature of the transported air and achieve the effect of transporting warm air into the indoor space A to increase the indoor temperature therein. In another embodiment, the air-conditioner 26a can decrease the temperature of the transported air, and achieve the effect of transporting cold air into the indoor space A to decrease the indoor temperature. Since the air conditioner generator 26a can adjust the temperature of the indoor space A, the room temperature of the indoor space A can be adjusted to a preset temperature. In addition, the air-conditioner 26a has a dehumidification function to adjust the humidity of the indoor space A, so that the indoor space A can be adjusted to a preset humidity.

The above-mentioned purification unit 23 disposed in the gas-inlet channel 22 can be implemented in the combination of various embodiments. For example, the purification unit 23 includes a high efficiency particulate air (HEPA) filter screen 23a. When the gas is introduced into the gas-inlet channel 22 by the gas-inlet guider 24a, and the gas is filtered through the HEPA filter screen 23a to adsorb the chemical smoke, bacteria, dust particles and pollen contained in the gas to achieve the effects of filtering and purifying the gas. In some embodiments, the HEAP filter screen 23a is coated with a cleansing factor containing chlorine dioxide to inhibit viruses, bacteria, influenza A virus, influenza B virus, enterovirus or norovirus in the gas outside the gas exchanger 2. The inhibition rate can reach more than 99%. It is helpful of reducing the cross-infection of viruses. In other embodiments, the HEPA filter screen 23a is coated with a herbal protective layer extracted from ginkgo and Japanese *Rhus chinensis* to form a herbal protective anti-allergic filter, so as to resist allergy effectively and destroy a surface protein of influenza virus, such as H1N1 influenza virus, in the gas introduced by the gas exchanger 2 and passing through HEPA filter screen 23a. In some other embodiments, the HEPA filter screen 23a is coated with a silver ion to inhibit viruses and bacteria contained in the gas introduced by the gas exchanger 2.

In an embodiment, the purification unit 23 includes a photo-catalyst unit 23b combined with the HEPA filter screen 23a. The photo-catalyst unit 23b includes a photo-catalyst 231b and an ultraviolet lamp 232b. The photo-catalyst 231b is irradiated with the ultraviolet lamp 232b to decompose the gas introduced by the gas exchanger 2 for filtering and purifying, so as to purify the gas. In the embodiment, the photo-catalyst 231b and the ultraviolet lamp 232b are disposed in the gas-inlet channel 22, respectively, and spaced apart from each other at a distance. In the embodiment, the outdoor gas is introduced into the gas-inlet channel 22 by the gas-inlet guider 24a, and the photo-catalyst 231b is irradiated by the ultraviolet lamp 232b to convert light energy into chemical energy, thereby decomposes harmful gases and disinfects bacteria contained in the gas, so as to achieve the effects of filtering and purifying the introduced gas.

In an embodiment, the purification unit 23 includes a photo-plasma unit 23c combined with the HEPA filter screen 23a. The photo-plasma unit 23c includes a nanometer irradiation tube. The gas introduced by the gas exchanger 2 is irradiated by the nanometer irradiation tube to decompose volatile organic gases contained in the gas and purify the gas. In the embodiment, the nanometer irradiation tube is disposed in the gas-inlet channel 22. When the outdoor gas is introduced into the gas-inlet channel 22 by the gas-inlet guider 24a, the gas is irradiated by the nanometer irradiation tube, thereby decomposes oxygen molecules and water molecules contained in the gas into high oxidizing photo-plasma, which is an ion flow capable of destroying organic molecules. In that, volatile formaldehyde, volatile toluene and volatile organic (VOC) gases contained in the gas are decomposed into water and carbon dioxide, so as to achieve the effects of filtering and purifying the introduced gas.

In an embodiment, the purification unit 23 includes a negative ionizer 23d combined with the HEPA filter screen 23a. The negative ionizer 23d includes at least one electrode wire 231d, at least one dust collecting plate 232d and a boost power supply device 233d. When a high voltage is discharged through the electrode wire 231d, the suspended particles contained in the gas introduced by the gas exchanger 2 are attached to the dust collecting plate 232d, so as to purify the gas. In the embodiment, the at least one electrode wire 231d and the at least one dust collecting plate 232d are disposed within the gas-inlet channel 22. When the at least one electrode wire 231d is provided with a high voltage to discharge, the dust collecting plate 232d is carry with negative charge. When the outdoor gas is introduced into the gas-inlet channel 22 by the gas-inlet guider 24a, the at least one electrode wire 231d discharges to make the suspended particles in the gas to carry with positive charge, and therefore the suspended particles having positive charge are adhered to the dust collecting plate 232d carry with negative charges, so as to achieve the effects of filtering and purifying the introduced gas.

In an embodiment, the purification unit 23 includes a plasma ion unit 23e combined with the HEPA filter screen 23a. The plasma ion unit 23e includes a first electric-field protection screen 231e, an adsorption filter screen 232e, a high-voltage discharge electrode 233e, a second electric-field protection screen 234e and a boost power supply device 235e. The boost power supply device 235e provides a high voltage to the high-voltage discharge electrode 233e to discharge and form a high-voltage plasma column with plasma ion, so that the plasma ion of the high-voltage plasma column decomposes viruses or bacteria contained in the gas introduced by the gas exchanger 2. In the embodiment, the first electric-field protection screen 231e, the adhering filter screen 232e, the high-voltage discharge electrode 233e and the second electric-field protection screen 234e are disposed within the gas-inlet channel 22. The adhering filter screen 232e and the high-voltage discharge electrode 233e are located between the first electric-field protection screen 231e and the second electric-field protection screen 234e. As the high-voltage discharge electrode 233e is provided with a high voltage by the boost power supply 235e, a high-voltage plasma column with plasma ion is formed. When the outdoor gas is introduced into the gas-inlet channel 22 by the gas-inlet guider 24a, oxygen molecules and water molecules contained in the gas are decomposed into positive hydrogen ions ($H^+$) and negative oxygen ions ($O_2^-$) through the plasma ion. The substances attached with water around the ions are adhered on the surface of viruses and bacteria and converted into OH radicals with extremely strong oxidizing power, thereby removing hydrogen (H) from the protein on the surface of viruses and bacteria, and thus decomposing (oxidizing) the protein, so as to filter the introduced gas and achieve the effects of filtering and purifying.

Notably, the purification unit 23 can only include the HEPA filter screen 23a, or includes the HEPA filter screen 23a combined with any one of the photo-catalyst unit 23b, the photo-plasma unit 23c, the negative ionizer 23d and the plasma ion unit 23e. In an embodiment, the purification unit 23 includes the HEPA filter screen 23a combined with any two of the photo-catalyst unit 23b, the photo-plasma unit 23c, the negative ionizer 23d and the plasma ion unit 23e. Alternatively, the HEPA filter screen 23a combined with any three of the photo-catalyst unit 23b, the photo-plasma unit 23c, the negative ionizer 23d and the plasma ion unit 23e. In other embodiment, the purification unit 23 includes the HEPA filter screen 23a combined with all of the photo-catalyst unit 23b, the photo-plasma unit 23c, the negative ionizer 23d and the plasma ion unit 23e.

Preferably but not exclusively, the gas-inlet guider 24a is a fan, such as a vortex fan or a centrifugal fan. Preferably but not exclusively, the gas-outlet guider 24b is a fan, such as a vortex fan or a centrifugal fan. Notably, in the above embodiments, the gas-inlet guider 24a and the gas-outlet guider 24b can be enabled or disabled by the remote-control driving device 25. In addition to the individual control of the enablement or disablement of the gas-inlet guider 24a and the gas-outlet guider 24b, the exported airflow rate of the gas-inlet guider 24a and the gas-outlet guider 24b can also be individually controlled during operation, and the exported airflow rate can be ranged from 200 CADR to 1600 CADR.

Figure 11:
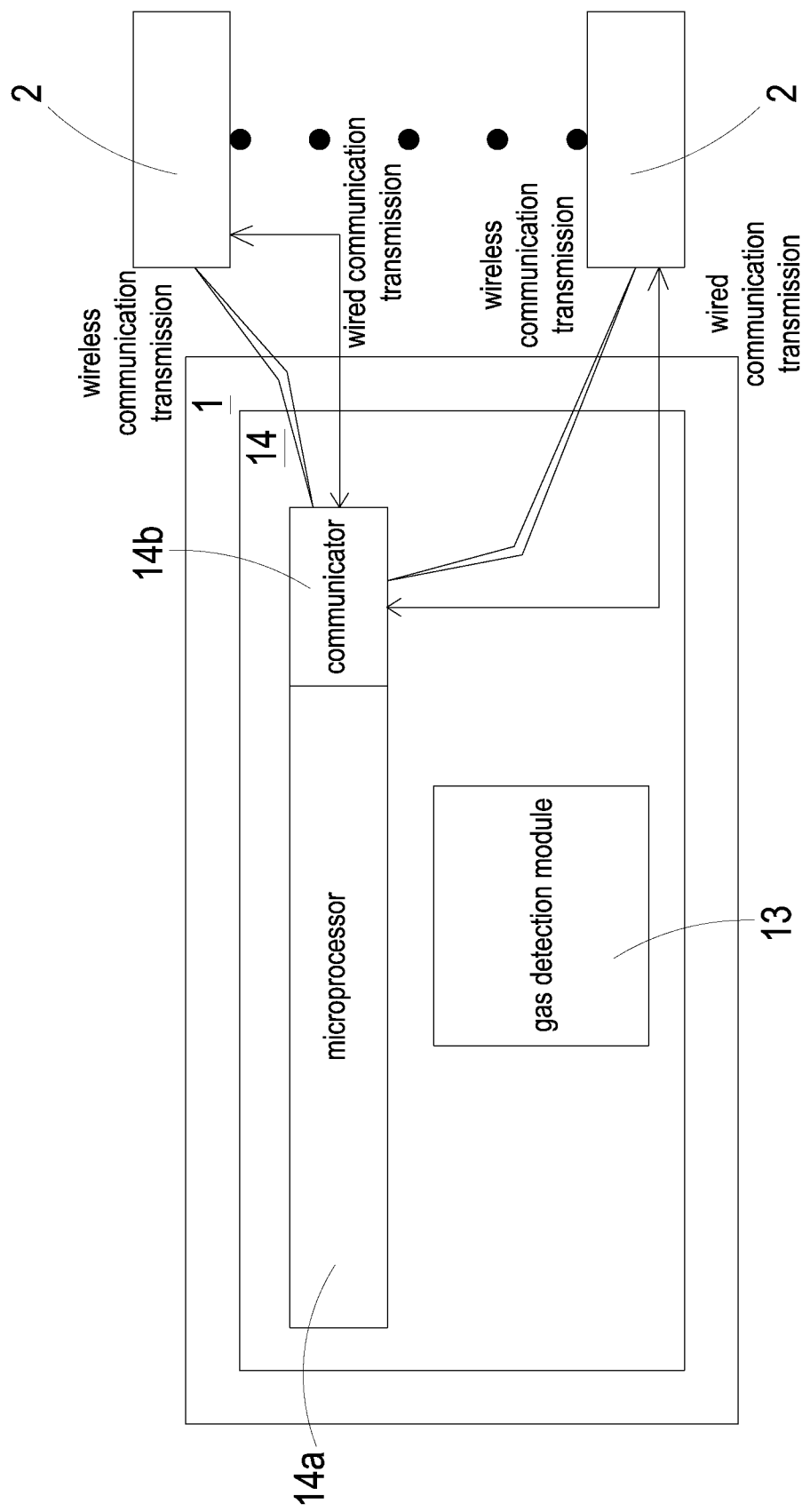
FIG. 11 is a block diagram illustrating a configuration of a controlling circuit board and the gas exchanger for implementing the method of preventing and handling indoor air pollution according to the embodiment of the present disclosure.

Please refer to FIG. 11. In the embodiment, the portable gas detection device 1 further includes a controlling circuit unit, 14. A microprocessor 14a and a communicator 14b are disposed on the controlling circuit unit 14, and the gas detection module 13 is electrically connected to the controlling circuit unit 14. The microprocessor 14a controls a driving signal of the gas detection module 13 to enable the detecting operation, and converts a detection datum of the gas detection module 13 into detection information for storing. The communicator 14b receives the detection information outputted by the microprocessor 14a, and externally transmits the detection information to the gas exchangers 2 through a communication transmission, so as to control the actuation of the gas exchangers 2 and adjust the exported airflow rate of the gas exchangers 2. Thus, the purified gas is exported to the indoor space A within 1~10 minutes for exchanging the air pollutant, so as to reduce the air pollutant to the safe detection value, for example, PM2.5 is less than 10 μg/m$^3$, such that the gas in the indoor room A is exchanged into a safe and breathable condition. Preferably but not exclusively, the communication transmission of the communicator 14b may be a wired two-way communication transmission, such as a USB communication transmission, or a wireless two-way communication transmission, such as Wi-Fi communication transmission, Bluetooth communication transmission, a radio frequency identification communication transmission, or a near field communication (NFC) transmission.

Notably, a signal is transmitted between the communicator 14b and the at least one gas exchanger 2. The transmitted signal can automatically adjust the exported airflow rate and the number of the online gas exchangers through the microprocessor 14a based on the pre-determined size of the indoor space A and the desired operation time required to reduce the air pollutant to the safe detection value, but not limited thereto. Besides automatically and/or modularly settings, the indoor space A, the operation time for reducing the air pollutant to the safe detection value, the exported airflow rate of the gas exchanger 2, and the number of the online gas exchangers can also be set manually and individually.

Figure 12:
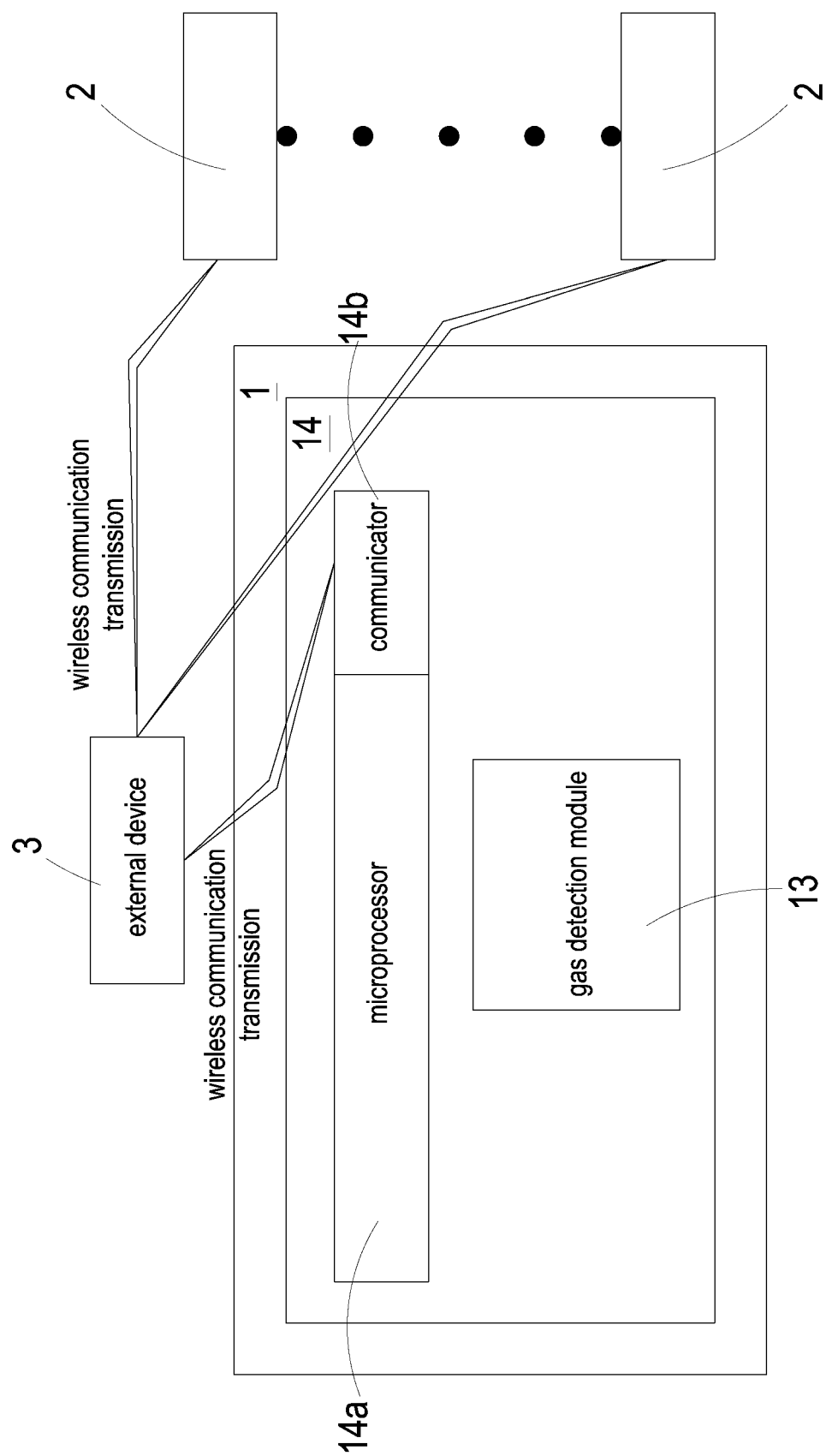
FIG. 12 is a block diagram illustrating a configuration of a controlling circuit board, an external device and the gas exchanger for implementing the method of preventing and handling indoor air pollution according to the embodiment of the present disclosure.

Please refer to FIG. 12. In the embodiment, the portable gas detection device 1 further includes a controlling circuit unit, 14. A microprocessor 14a and a communicator 14b are disposed on the controlling circuit unit 14, and the gas detection module 13 is electrically connected to the controlling circuit unit 14. The microprocessor 14a controls a driving signal of the gas detection module 13 to enable the detecting operation, and converts a detection datum of the gas detection module 13 into detection information for storing. The communicator 14b receives the detection information outputted by the microprocessor 14a, and externally transmitted the detection information to an external device 3 through a communication transmission for storing, so that the external device 3 can generate a gas detection information and an alarm, and the external device 3 can control the actuation of the gas exchangers 2 and adjusts the exported airflow rate of the gas exchangers 2. Preferably but not exclusively, the external device 3 is a portable mobile device.

Notably, the communicator 14b transmits a signal to the at least one gas exchanger 2 through the external device 3. The transmitted signal can automatically adjust the exported airflow rate and the number of the online gas exchangers through the microprocessor 14a based on the pre-determined size of the indoor space A and the desired operation time required to reduce the air pollutant to the safe detection value, but not limited thereto. Besides automatically and/or modularly settings, the indoor space A, the operation time for reducing the air pollutant to the safe detection value, the exported airflow rate of the gas exchanger 2, and the number of the online gas exchangers can also be set manually and individually.

In summary, the present disclosure provides a method of preventing and handling indoor air pollution. The portable gas detection device 1 is utilized to monitor the air quality in the indoor space A at any time, and the purification unit 23 provides solutions of purifying and improving the air quality. In that, the gas detection module 13 and the purification unit 23 combined with the gas guider 24 can export a gas at a specific airflow amount, so as to allow the purification unit 23 to filter and obtain a purified gas. In addition, the gas guider 24 constantly controls the exported airflow rate ranged from 200~1600 clean air output ration (CADR) within 10 minutes, and 1~50 gas exchangers 2 are provided for implementation in the indoor space A, so that the air pollution in the indoor space A is reduced to a safe detection value, and the gas is exchanged into a safe and breathable condition. Moreover, the real-time information is available for issuing an alarm, so as to allow people to take the measures for preventing and handling indoor air pollution immediately.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method of preventing and handling indoor air pollution for an indoor space, comprising:
   a) providing a portable gas detection device and at least one gas exchanger for implementing in the indoor space, wherein the portable gas detection device can be carried by a user, and the portable gas detection device comprises a main body, and the main body comprises at least one inlet, at least one outlet and a gas detection module, the gas detection module is disposed in the main body and comprises a base, a piezoelectric actuator, a laser component and at least one sensor, wherein the piezoelectric actuator, laser component and the at least one sensor are accommodated in the base, and the at least one sensor includes a particulate sensor, the at least one gas exchanger is allowed to inhale an outdoor gas, purify and filter the inhaled gas, and introduce the inhaled gas into the indoor space, wherein an air pollutant in the indoor space is exchanged and exported out to the outdoor environment;
   b) disposing 1 to 50 gas exchangers within the indoor space, wherein the at least one gas exchanger has an exported airflow rate ranged from 200 clean air delivery rate (CADR) to 1600 CADR, and the indoor space has a volume of 247.5~1650 m3; and
   c) remotely controlling at least one of the gas exchangers to enable filtration, purification and gas exchange procedure by the portable gas detection device, as the portable gas detection device detects an air pollutant in the indoor space in real time, to reduce the air pollutant in the gas in the indoor space to a safe detection value within 10 minutes, so that the air pollutant in the indoor space can be exchanged and purified.

2. The method of preventing and handling indoor air pollution according to claim 1, wherein the safe detection value is selected from the group consisting of PM2.5 less than 10 μg/m3, carbon dioxide content less than 1000 ppm, total volatile organic compounds (TVOC) less than 0.56 ppm, formaldehyde content less than 0.08 ppm, the amount of bacteria less than 1500 CFU/m3, the amount of fungi less than 1000 CFU/m3 and a combination thereof.

3. The method of preventing and handling indoor air pollution according to claim 1, wherein the exported airflow rate of the at least one gas exchanger is 800 CADR, the volume of the indoor space is ranged from 247.5 to 1650 m3, and 2 to 13 gas exchangers are disposed in the indoor space.

4. The method of preventing and handling indoor air pollution according to claim 1, wherein the air pollutant in the indoor space is one selected from the group consisting of PM1, PM2.5, PM10, carbon dioxide, TVOC, formaldehyde, bacteria, virus and a combination thereof.

5. The method of preventing and handling indoor air pollution according to claim 1, wherein the at least one sensor comprises a gas sensor, and the gas sensor is accommodated in the base, and the gas outside the main body is introduced by the piezoelectric actuator, so that the gas is inhaled through the at least one inlet, discharged out through the at least one outlet, and introduced into the at least one sensor for detecting and obtaining gas information.

6. The method of preventing and handling indoor air pollution according to claim 5, wherein the sensor of the gas detection module comprises a volatile organic compound sensor for detecting and obtaining the gas information of CO2 or TVOC.

7. The method of preventing and handling indoor air pollution according to claim 5, wherein the sensor of the gas detection module comprises a formaldehyde sensor for detecting and obtaining the gas information of formaldehyde.

8. The method of preventing and handling indoor air pollution according to claim 1, wherein the particulate sensor is for detecting and obtaining the gas information of PM1, PM2.5 or PM10.

9. The method of preventing and handling indoor air pollution according to claim 1, wherein the sensor of the gas detection module comprises a pathogenic bacteria sensor for detecting and obtaining the gas information of bacteria or pathogenic bacteria.

10. The method of preventing and handling indoor air pollution according to claim 1, wherein the portable gas detection device further comprises a controlling circuit unit with a microprocessor and a communicator disposed thereon, and the gas detection module is electrically connected to the controlling circuit unit, wherein the microprocessor controls a driving signal of the gas detection module to enable the detecting operation, and convert a detection datum of the gas detection module into detection information for storing, wherein the communicator receives the detection information outputted by the microprocessor, and externally transmits the detection information to the gas exchangers through a wired or a wireless communication transmission, so as to control an actuation of the gas exchangers and adjust the exported airflow rate of the gas exchangers.

11. The method of preventing and handling indoor air pollution according to claim 1, wherein the portable gas detection device further comprises a controlling circuit unit with a microprocessor and a communicator disposed thereon, and the gas detection module is electrically connected to the controlling circuit unit, wherein the microprocessor controls a driving signal of the gas detection module to enable the detecting operation, and convert a detection datum of the gas detection module into detection information for storing, wherein the communicator receives the detection information outputted by the microprocessor, and externally transmits the detection information to an external device for storing, so that the external device generates a gas detection information, and the external device controls an actuation of the gas exchangers and adjusts the exported airflow rate of the gas exchangers.

12. The method of preventing and handling indoor air pollution according to claim 11, wherein the external device is a portable mobile device.

13. The method of preventing and handling indoor air pollution according to claim 1, wherein each of the at least one gas exchanger comprises a gas-inlet channel, a gas-outlet channel, a purification unit and a remote-control driving device.

14. The method of preventing and handling indoor air pollution according to claim 13, wherein each of the at least one gas exchanger further comprises at least one gas guider, wherein the portable gas detection device detects the air pollutant in the indoor space, a control signal is transmitted to the remote-control driving device, so that the gas is inhaled from the outdoor environment into the gas exchanger through the gas guider, transported through the gas inlet channel, purified and filtered by the purification unit, and then introduced into the indoor space, and the air pollutant in the indoor space is exported out to the outdoor environment through the gas-outlet channel.

15. The method of preventing and handling indoor air pollution according to claim 13, wherein each of the at least one gas exchanger further comprises a plurality of gas guiders, and the plurality of gas guiders comprises a gas-inlet guider and a gas-outlet guider, wherein the portable gas detection device detects the air pollutant in the indoor space, a control signal is transmitted to the remote-control driving device, so that the gas is inhaled from the outdoor environment into the gas exchanger through the gas-inlet guider, transported through the gas inlet channel, purified and filtered by the purification unit, and then introduced into the indoor space, and the air pollutant in the indoor space is exported out to the outdoor environment through the gas-outlet channel by the gas-outlet guider.

16. The method of preventing and handling indoor air pollution according to claim 13, wherein each of the at least one gas exchanger further comprises an air-conditioner, wherein when the portable gas detection device detects the air pollutant in the indoor space, a control signal is transmitted to the remote-control driving device, so that the gas is inhaled from the outdoor environment into the gas exchanger through the air-conditioner, transported through the gas inlet channel, purified and filtered by the purification unit, adjusted the temperature and humidity thereof by the air-conditioner, and then introduced into the indoor space, and the air pollutant in the indoor space is exported out to the outdoor environment through the gas-outlet channel.

17. The method of preventing and handling indoor air pollution according to claim 13, wherein the purification unit is a high efficiency particulate air filter screen.

18. The method of preventing and handling indoor air pollution according to claim 17, wherein the high efficiency particulate air filter screen is coated with a cleansing factor containing chlorine dioxide to inhibit viruses and bacteria in the gas.

19. The method of preventing and handling indoor air pollution according to claim 17, wherein the high efficiency particulate air filter screen is coated with a silver ion to inhibit viruses and bacteria contained in the gas introduced into the main body.

20. The method of preventing and handling indoor air pollution according to claim 17, wherein the purification unit is combined with photo-catalyst unit, a photo-plasma unit, a negative ionizer, a plasma ion unit, or a combination thereof.

* * * * *